(12) United States Patent  
Richardson

(10) Patent No.: US 8,311,312 B1  
(45) Date of Patent: Nov. 13, 2012

(54) APPARATUS, SYSTEMS AND METHODS FOR ACCEPTING OR REJECTING A MANUFACTURED MEDICAL DEVICE

(75) Inventor: Andrew J. Richardson, Nenagh (IE)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 353 days.

(21) Appl. No.: 12/466,276

(22) Filed: May 14, 2009

(51) Int. Cl.  
*G06K 9/00* (2006.01)

(52) U.S. Cl. ........................................ 382/141

(58) Field of Classification Search ............... 382/141, 382/152; 623/912  
See application file for complete search history.

(56) References Cited

U.S. PATENT DOCUMENTS

| | | | | |
|---|---|---|---|---|
| 6,606,403 | B2* | 8/2003 | Freifeld | 382/152 |
| 2003/0118230 | A1* | 6/2003 | Song et al. | 382/152 |
| 2005/0177264 | A1* | 8/2005 | Lin et al. | 700/110 |
| 2008/0311281 | A1 | 12/2008 | Andreacchi et al. | |
| 2008/0312747 | A1 | 12/2008 | Cameron et al. | |
| 2010/0014747 | A1* | 1/2010 | Freifeld | 382/141 |

* cited by examiner

*Primary Examiner* — Tarifur Chowdhury  
*Assistant Examiner* — Jonathan Hansen  
(74) *Attorney, Agent, or Firm* — Squire Sanders (US) LLP

(57) ABSTRACT

A inspection system for medical devices includes an inspection station, a workstation and a database. The inspection system collects images of the medical device. Analysis of the images reveals whether there is a defect in the medical device. If there is a defect, then a comparison analysis is performed between the defect and information in the database. The comparison analysis produces an indication of whether the medical device should be rejected in view of the defect or accepted in spite of the defect.

8 Claims, 18 Drawing Sheets

APPARATUS, SYSTEMS AND METHODS FOR ACCEPTING OR REJECTING A MANUFACTURED MEDICAL DEVICE

BACKGROUND OF THE INVENTION

1. Field of the Invention

The present invention relates to inspection of manufactured medical devices; more particularly, this invention relates to automated detection and evaluation of defects in manufactured medical devices.

2. Background of the Invention

The inspection of medical devices can be a labor intensive process. One particular area where there is a substantial amount of manual labor required for inspection is the inspection of self-expanding or balloon-expandable stents. These devices must be carefully inspected by a technician during various stages of manufacture, including when they are cut from tubes, for example, or when a drug-eluting coating is applied. The inspection process is laborious and time-consuming for both metal and polymer stent types. The later category, in particular, requires close inspection due to, e.g., the susceptibility of failure when a micro-crack appears in a polymer strut. Typically, the inspection process involves the viewing of the surfaces of a manufactured stent under a microscope by a technician, who decides whether the stent should be rejected or accepted based on his/her own judgment.

On the one hand, a stent will usually have one or more defects, but in many cases these defects are negligible. On the other hand, a defect may seem innocuous but upon closer inspection there appears a potentially serious problem with the stent, e.g., a micro crack appearing in a high stress region of a polymer stent. The stent is accepted in spite of the defect, in the former case, and rejected as unusable in the later case.

Since the days when clinical side-effects resulting from defective stents were first reported, a thorough stent inspection standard has been adopted throughout the industry. To the inventor's knowledge this stent inspection is still performed manually by a technician hunched over a microscope inspecting every surface of a stent. Despite this inefficiency, the art has yet to produce a satisfactory solution to the inspection problem for medical devices.

It is critical to determine whether there are defects, which requires expertise in being able to visually spot defects that appear only at the microscopic level, e.g., a micro-crack in a stent, coating irregularity, etc. Stents have complex patterns of interacting structural members and measure in lengths of millimeters. Moreover, not all defects will cause problems. The challenge is, therefore, not simply a matter of finding a defect. Rather, the industry requires one to differentiate between defects that are likely to cause problems verses defects that may be ignored, so that usable stents are not disregarded needlessly due to a minor defect.

SUMMARY OF THE INVENTION

In view of the foregoing problems that have remained unsolved in the art, the invention provides an apparatus, system and method for automated inspection of medical devices. Solutions are disclosed that can significantly reduce the man hours that the art has come to accept as necessary in order to properly qualify a medical device for use.

It has been found that there are certain re-occurring traits that are dispositive of whether a defect is acceptable or not acceptable when a medical device is inspected. From this discovery, it has been further discovered that the reoccurring traits are amenable to one or more computer-implemented methods or algorithms. As such, when these traits can be identified in a stent defect, the defect may be inspected by an automated process. The traits may be expressible as a spatial quantity that is tied to analysis of a model, e.g., a Finite Element Model (FEM) or drug release model, a property of material, e.g., brittleness of a polymer and other properties.

According to a system constructed in accordance with some aspects of the invention, as embodied in a stent inspection system, a station collects images of the stent. Then the images are processed into one or more datasets, which include categorizing information, header information, and/or metadata that allows the defect information to be queried against known defect information stored in a relational database. From this query information knowledge is made available as to the types of defects that have been accepted or not accepted, which enables decision-making in an automated fashion, manually, or combination automated-manual basis as will be appreciated. One or more criterion or logic may be implemented, as will also be appreciated upon a perusal of the disclosure.

According to one aspect of the invention, a computer-based method for inspecting a medical device includes (a) collecting images showing a portion of the medical device; (b) finding a defect in the portion by computer analysis of the collected images; (c) retrieving samples of previously-inspected medical devices that were rejected or accepted in spite of defects; and (d) comparing the found defect to the prior found defect including computing at least one number and, based on this comparison, deciding whether to accept, reject or manually inspect the medical device.

According to another aspect of the invention, an apparatus for inspecting a manufactured medical device having a longitudinal axis includes a mechanism configured to articulate the medical device about at least the longitudinal axis; a camera configured to operate in such a manner as to enable the generation of a plurality of images of the medical device in synchronization with a predetermined operating sequence of the mechanism; and an image processor for producing processed images of the manufactured medical devices in response to receiving the plurality of images, the image processor further including an analyzer which computes a value based on information contained in at least the processed images and, based on at least the one value produces an indication of whether the medical device should be accepted or rejected.

The medical device may be a scaffolding stent cut from a tube by a laser, the stent having a plurality of self expanding or balloon-expandable rings connected through longitudinal struts. A relational database may be constructed to catalog information about known defects, i.e., when acceptable or not acceptable, searchable according to the stent type, type of defect and/or location of the defect, the analyzer receiving as input material or process information from the database about known defects, and wherein if a defect is found in a stent strut or ring this defect is compared to at least one known strut or ring defect retrieved from the database and, based on this comparison, a predefined pass-fail logic is applied to provide as output the indication of whether the stent should be accepted or rejected.

According to another aspect of the invention a system for rejecting or accepting a self expanding or balloon expandable stent under inspection and having at least one defect includes processing a plurality of images of the stent surfaces including searching for a defect in the stent, and if a defect is found, providing a data set that includes information defining the stent type, the location on the stent where the defect was found, and a description of the defect; a knowledge base including a plurality records, each of the records defining a defect type and an indication of whether a previously inspected stent was rejected due to the presence of this defect or accepted in spite of this defect, the records being retrievable from the knowledge base in response to a input specifying one or more characteristic properties of the stent and location of where a defect was found; obtaining from the knowledge base a subset from the plurality of records, the subset being those records corresponding to the stent's type, location and/or type of found defect; and a computer for performing a comparison between the found defect and at least one of the subset of records, the computer program producing as output an indication that the stent should be rejected (or "scrapped"), held for further inspection or accepted in spite of the found defect.

According to another aspect of the invention there is a method, system and apparatus for detecting non-uniform drug-polymer coatings.

According to another aspect of the invention there is a method, system and apparatus for training personnel to identify defects in a medical device as acceptable or unacceptable.

According to another aspect a computer program product residing on a computer readable media contains a collection of programmable logic for deciding, or recommending whether a stent is acceptable based on input about a defect found in the stent. The computer program product may reside on an optical, solid state, or magnetic storage medium, non-volatile memory, volatile memory, for example.

According to another aspect of invention, there is a computer program product residing on computer readable media that provides one or more logical outcomes resulting from "if-then-else" type tests, structured to compare data produced from an inspected stent and data read from a knowledge base. The knowledge base, in this sense, may be an independently searchable database, but need not be in this aspect of invention. In one example, a comparison is made between length, width, height, volume, surface, areas, etc. data computed from digital image data and heuristic rules comprising a table of acceptance/rejection criteria for various defect types.

In one embodiment, the table consist of one or more of the criteria selected from the set consisting of: whenever a crack or fracture extends beyond a predefined length at or near a high stress area (i.e., a bend or crown) then the stent is rejected; when a surface area of the webbing extending between stent members is beyond a predefined surface area then the stent is rejected; when a strut touches another strut the stent is rejected; when bending causes a strut to extend beyond the abluminal stent surface by a predefined amount, the stent is rejected; when an opening in the coating exposes an underlying metal surface exceeds a specified acceptance criteria for an exposed surface, the stent is rejected; when a coating peels or tears, and is found to exceed an allowable size of tear/peel then the stent is rejected; when a polymer strand exceeds an allowable amount for a polymer strand the stent is rejected; when a rough surface finish exceeds the required level of smoothness needed for a surface, e.g., a metallic or polymer surface receiving a polymer coating, then the stent is rejected; when a foreign material is found in the base material that cannot be removed using an air gun, and exceeds an allowable size/volume then the stent is rejected; when a stent exhibits a sharp point/edge that exceeds a smoothness criteria then the stent is rejected; and when stent struts overlap the stent is rejected.

According to another aspect of the invention there is a method, system and apparatus for finding structural flaws in a medical device.

According to another aspect of the invention there is a method, system and apparatus for reducing the time spent inspecting a medical device including identifying characteristic flaws in a medical based on previously inspected medical devices and utilizing logic to assist in deciding whether a similar flaw should also be rejected or accepted.

According to another aspect of the invention there is a method, system and apparatus for performing quality control, or quality assurance during inspection of a medical device including comparing a preliminary conclusion against similar data retrievable from a relational database. The quality control/assurance may be implemented using database information concurrently with a manual inspection or after a medical device has been accepted despite the presence of flaws. In one example, a quality control flag is activated if a stent is accepted despite the presence of a bent strut having a magnitude that is statistically significant with regards to stents rejected when bending is above a threshold magnitude.

According to another aspect of the invention there is a method, system and apparatus for performing an inspection of a medical device using a computing platform and relational database. The method, system and apparatus utilizes one or more of statistics, logical constructs, or a combination thereof developed from information including past inspections of the medical device and programmable heuristics adopted by professionals when the medical device is inspected, numerical analysis using analytic models (such as models adapted for predicting behaviors such as stress-strain, fracture, drug-release profile or a combination thereof) and industry-adopted standards for acceptable/unacceptable flaws for a medical device to decide whether to accept/reject a flaw in a medical device, within a predefined tolerance or acceptance level. In some embodiments a three-standard-deviation likelihood that a manual inspection of a flaw would have resulted in acceptance or rejection of a flaw is computed. In some embodiments a factor of safety (e.g., multiple any observed crack length by factor of 2 when deciding whether to accept crack) is used in combination with a rejection/acceptance criteria. In some embodiments an expert system or, more generally, artificial intelligence is used to arrive at, or assist with reaching conclusions. In someone embodiments a combination of the foregoing techniques and data sources are made available in an integrated system in communication with one or more local or remote data sources.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

According to the following disclosure the medical device (s) that are inspected using an inspection system according to the invention are self-expanding or balloon-expandable drug-eluting stents that are intended to function as scaffolding for maintaining the integrity of vasculature. As will be appreciated by the foregoing, while the invention reveals certain, novel advantages applicable unique to addressing the labor intensive problems associated with inspecting scaffolding stents during manufacture it is expected that the teaching may be readily adapted to inspection of other types of medical devices, such as certain types of catheters.

A system for inspecting manufactured stents follows. The inspection system is intended to operate as a stand alone system, or as a component of a larger processing line for verifying whether a stent (or stents) is/are free from unacceptable defects as they complete a manufacturing stage. In the examples that follow the two stages of interest are the forming stage and coating stage. In one embodiment the system is configured to operate in a batch mode following a stent forming or coating phase of manufacture. In another embodiment, the system is operated by a technician residing at a local control console, e.g., a personal computer or workstation.

Figure 1:
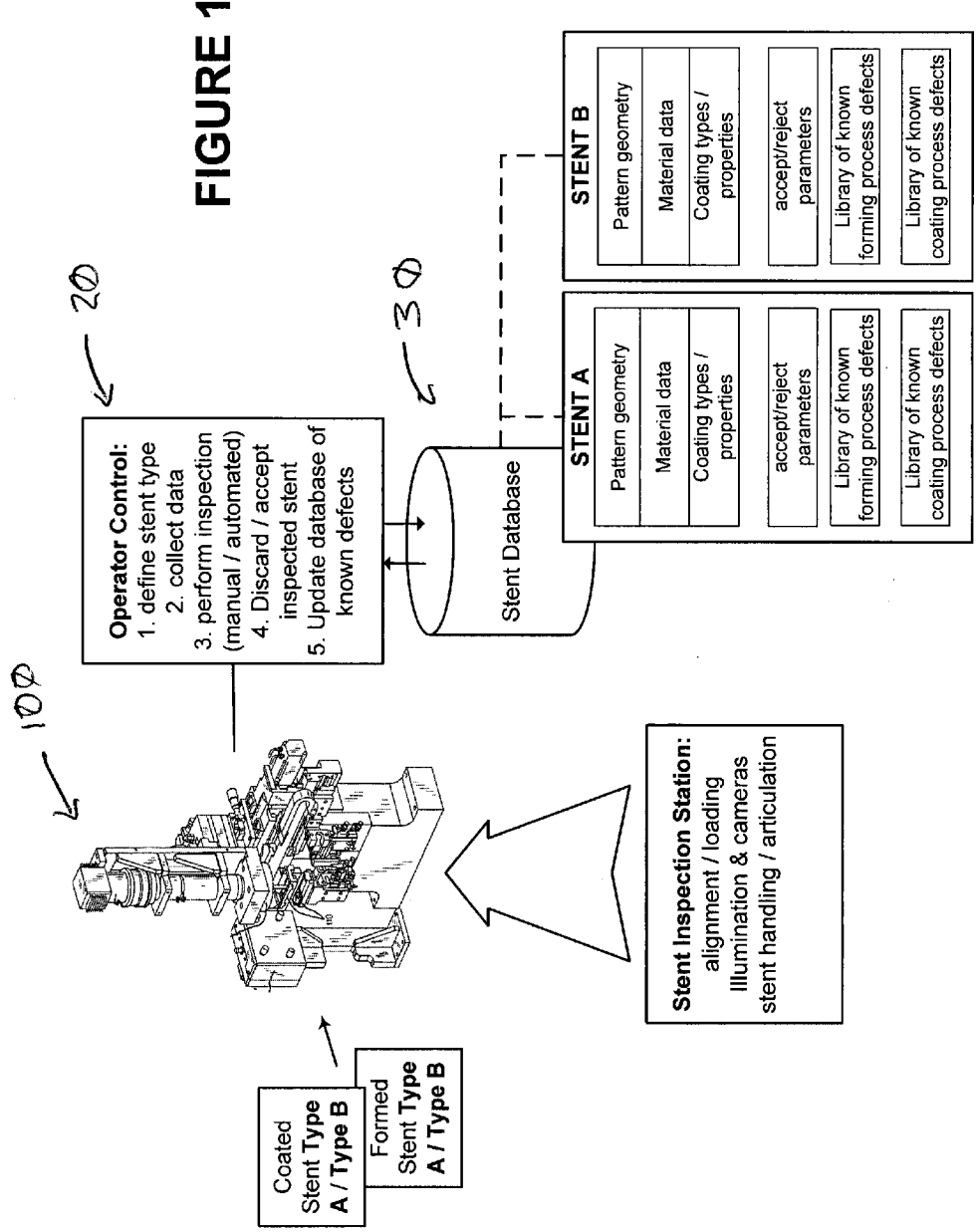
FIG. 1 is diagram illustrating aspects of a stent inspection system.

One embodiment of the foregoing inspection system is depicted in FIG. 1. An inspection system includes a inspection station 100, which includes a loading mechanism, imaging component and handling component. The loading component transfers the stent to a holding area, e.g., a mandrel assembly, and aligns it with a datum for the camera. The imaging component includes one or more cameras that obtain digital images of surfaces of a stent under inspection. The digital images are used to perform subsequent pattern matching for identifying defects. The defects are then analyzed to determine whether to reject the stent based on defects, or accept the stent despite the presence of defects. The handling component articulates the stent relative to a bore site for one or more strategically placed cameras. Using this close-cooperation between handling and imaging, which may be programmable or hardware-coded, a comprehensive digital map of stent surfaces may be obtained.

The inspection station 100 is in communication with, and controlled by a nearby computer 20, e.g., a personal computer. The computer 20 is in communication with at least one storage area 30 for storing information relating to the inspection of stents and comparing previously inspected stents with stents currently under inspection. In this comparison the inspection system lends itself to partial or full automation for stent inspection. A comparison between defects previously accepted and defects previously rejected, and images for a current, detected defect found in a stent may be undertaken numerically, e.g., computing probabilities based on generated statistics, applying a set of heuristic rules, or a combination of these. As a result, a significant number of man hours spent performing manual inspections of stents may be avoided.

The inspection station 100 receives a stent that has completed a manufacturing stage, such as a stent recently formed from a tube or coated with a drug-containing polymer coating, referred to in FIG. 1 as "formed stent" and "coated stent", respectively. The coated or formed stent are referred to as either a "Type A" or "Type B" stent. A Type A/B stent may designate stents of different lengths, geometry and/or coatings. Information about the Type A or Type B stent received at the inspection station 100 may be stored in the storage area 30 for retrieval by the computer 20, or stored locally in a memory device at the computer 20. This information may be used to assist with image processing, such as to align the stent with a camera or to identify defects from the obtained images.

Figure 2A:
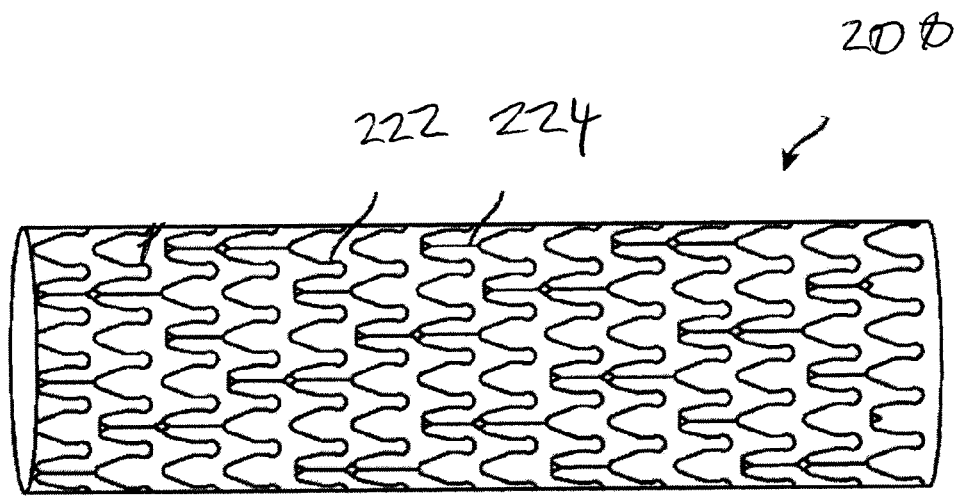
FIGS. 2A and 2B are side and isometric views of a balloon-expandable stent.
Figure 2B:
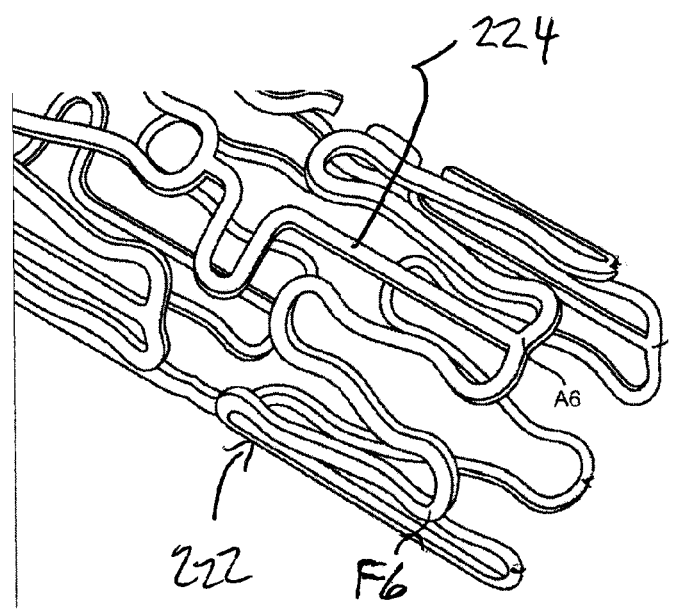

Referring to FIGS. 2A-2B, an example of a scaffolding stent 200, in this case balloon expandable, is shown. may be described as having longitudinally extending struts or links 224 extending between and connecting undulating or sinusoidal-like ring structures 222. The pattern for a stent when it is in its delivery configuration is shown. The ring structures provide radial stiffness when the stent diameter is expanded by a balloon, i.e., when the undulations straightened. The links 224, on the other hand, provide comparatively less stiffness, as can be appreciated by there being only a few disposed between rings 222 and carry loads through essentially slender bar-like bending stiffness. Hence, the stent structure is designed to provide radial stiffness and longitudinal flexibility. Other stiffness/strength properties of this structure will be appreciated by inspection of a stent's pattern, such as stress distributions when the structure is subjected to various types of static loads, recoil, local stiffness characteristics. Additionally, it will be appreciated that the ramifications of defects, e.g., cracks, in this structure must be treated differently when the stent is made from a metal vs. a polymer.

The arrangement of struts/links and rings depicted in FIGS. 2A-2B is formed from a tube using a laser. The laser is programmed to follow a pre-defined pattern reflecting the structure illustrated in FIGS. 2A-2B. A laser traces out the pattern in the solid tube by vaporizing material in its path. Sometimes the laser may cause cracks and/or striations to form, which can compromise strength and stiffness along critical stent load paths. After this step, annealing may be performed, and other post-cutting processes in order to workout residual stresses or remove left over material. At this point, the stent is inspected to determine whether there are any imperfections. If the stent passes this stage of inspection, it then moves to the stent coating portion of the manufacture process. Here coatings of a solution including a polymer dissolved in a solvent are successively applied to one or more surfaces of a stent. The solution contains a drug intended to elute from the polymer when the stent is located at a treatment site. After this coating is applied, the stent is again inspected to determine whether the coating is uniform and sufficiently disposed over the stent surfaces.

The computer, workstation or user console 20 may be used to operate the loading, handling and imaging components for the stent, or these operations may be performed automatically when a signal is received at the inspection station that a stent is ready for inspection. The signal received by the station 100 may also include information about the stent, in which case data from a nearby storage area is retrieved, which provides the information needed to initiate an automated inspection process for the stent. Alternatively, this operation may be performed manually by operator input.

The computer 20 may include a processor, user input device, such as a keyboard and mouse, and monitor (not shown). The computer 20 hardware may be a standard personal computer having a microprocessor, DRAM, video card, hardware bus, removable memory and an operating system supporting software based applications and providing system resources for those applications, etc.

In one embodiment a software program resident in computer memory is interactive with a technician at the computer 20, and includes a menu system provided through a graphical user interface. This software, which may be built and implemented using well-known techniques, allows the technician to view one or more images, adjust parameters associated with image processing, database retrieval and performing computations. The software program enables viewing images, identifying defects and performing the inspection for the found defects.

Through a process to be described in greater detail below (FIG. 18), an operator may initiate an automated inspection followed by a manual inspection (if necessary). The process includes a comparison of the found defects with known defect information from prior stent inspections stored in the database 30. A computational engine residing on the computer 20 memory makes use of defect-related information in a relational database (stent database 30) that includes categorizations of stent defects according to where they were found, e.g., the stent type and location on the stent, and the nature of the defect, e.g., crack, irregular coating. This computational engine is used to spot defects that would be determined as unacceptable or acceptable if manually inspected by the operator using knowledge gained from previously inspected stents. Defects that cannot be resolved through this computational engine are flagged as defects requiring manual inspection.

The relational database 30 includes, in addition to the libraries of defects, other types of data to assist with identifying a defect from a series of images and for evaluating the severity of the defect. As such, the database 30 may include information about the materials associated with the inspected stent, where or how it will be used, how it was made, and/or what special parameters, rules or criterion should be used (e.g., a safety factor, a particularly sensitive region or portion of the stent where defects are not tolerated, etc.) when a defect is evaluated or images taken of the stent surfaces.

Figure 3:
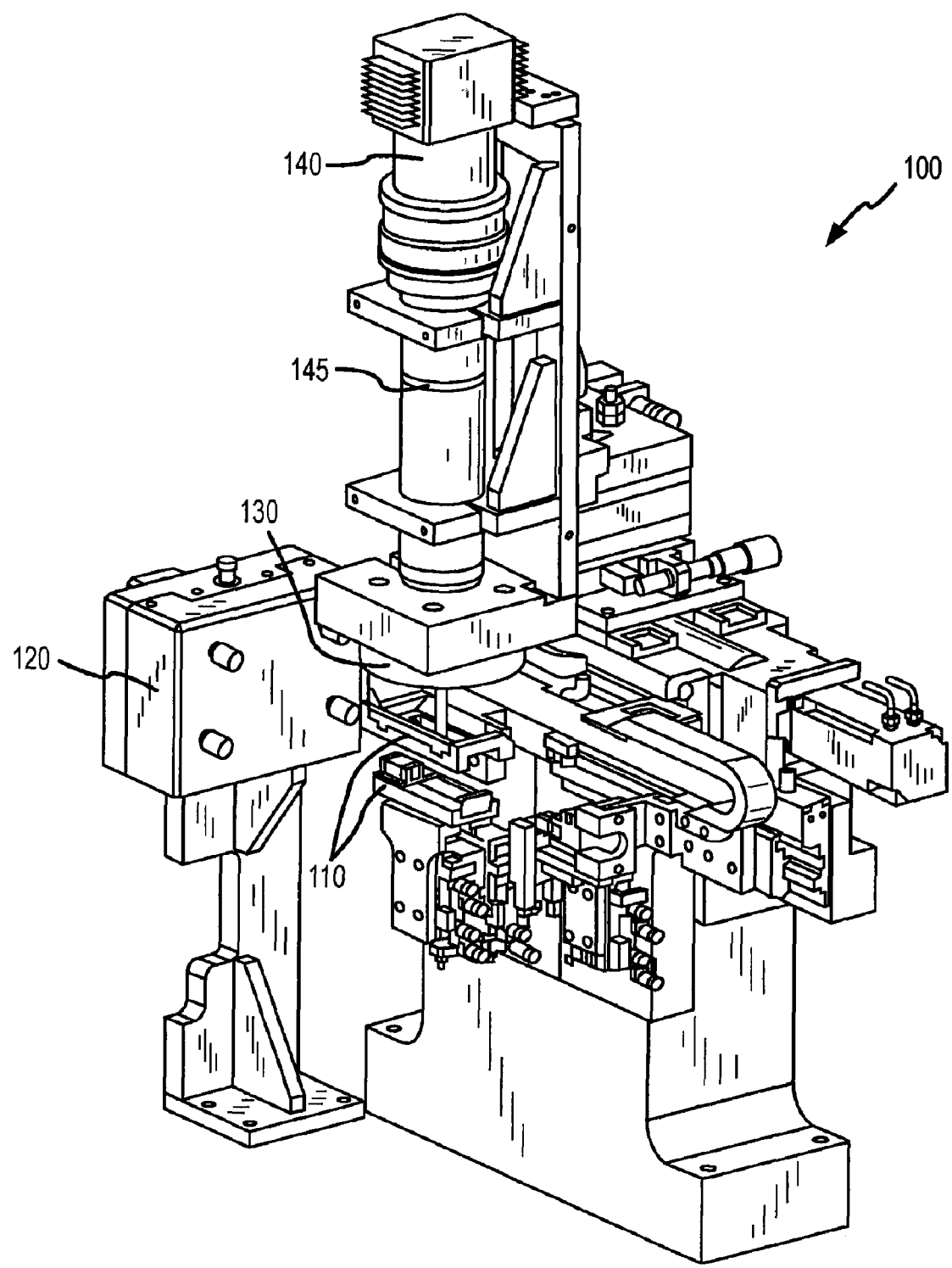
FIG. 3 is a stent inspection station.
Figure 4:
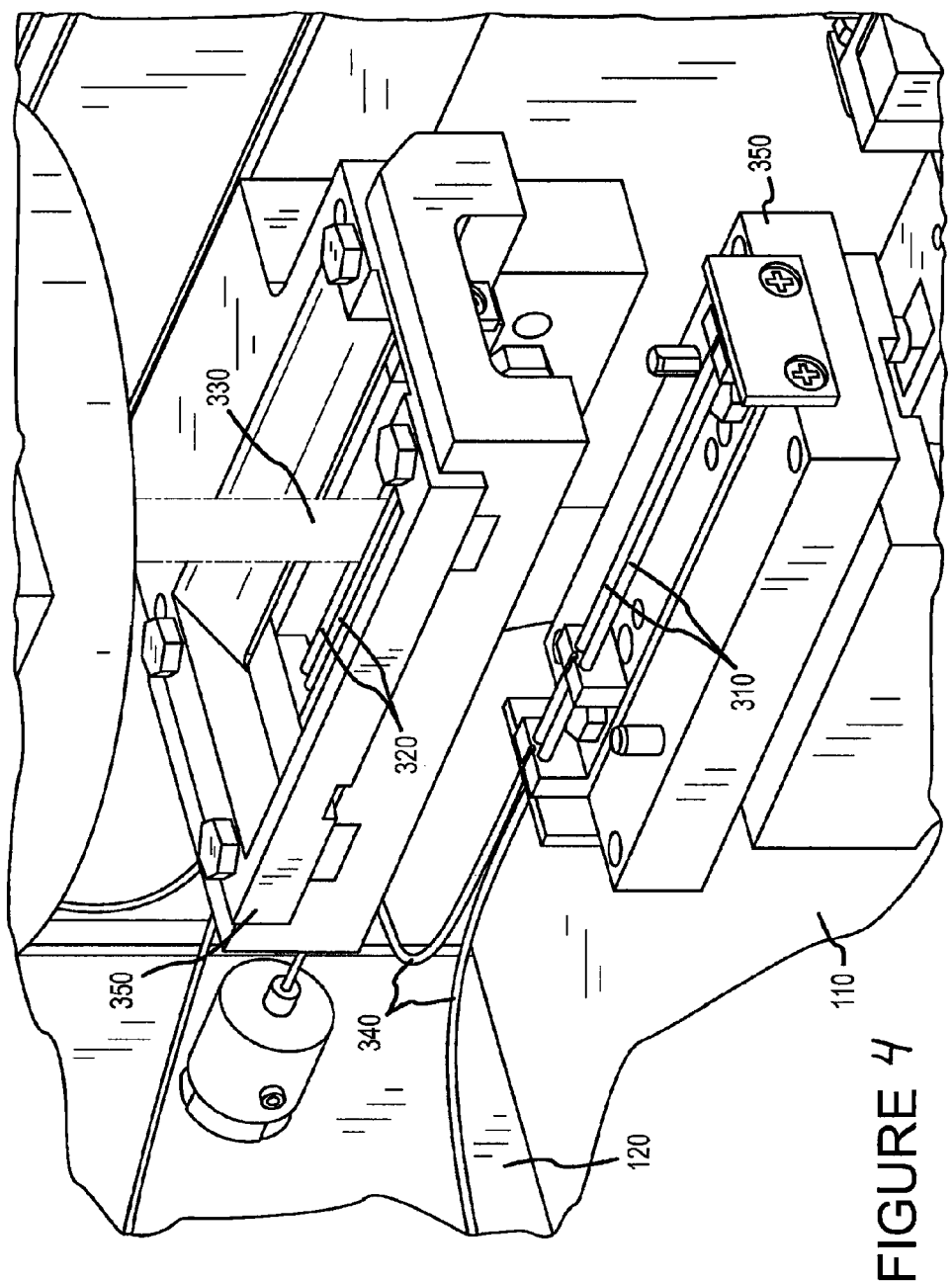
FIG. 4 is a perspective view of a portion of the inspection system of FIG. 1 showing a line of sight for a camera.

The following description makes reference to the handling and imaging of stent 200 by a stent inspection station. Referring now to FIGS. 3-4, the inspection station 100 according to one embodiment includes a roller assembly 110, a drive system 120, a light 130, and a camera 140. The roller assembly 110 holds the stent 200 in place and rotates the stent 200 about its longitudinal axis to allow the stent 200 to be imaged. The roller assembly 110 includes a lower pair of rollers 310 and an upper pair of rollers 320. The roller assembly 110 may be configured to allow the upper rollers 320 to rise to allow a stent 200 to be placed between the two lower rollers 310, then drop down to cradle the stent 200 between the four rollers 310, 320. Similarly, the lower rollers 310 may be configured to drop down to allow the loading and unloading of the stent 200, then rise up to allow the stent 200 to be cradled by the four rollers 310, 320. The rollers 310, 320 may be supported by bearing blocks 350 that may be configured to move up and down to allow loading and unloading of the stent 200. The roller pairs 310, 320 may be of suitable length and width to hold a stent 200 for imaging, and may include a gap 410 between two pairs of rollers 310, 320 to allow a camera 140 to view the stent 200 (not shown). As depicted in FIGS. 3 and 4, the camera's 140 field of view 330 passes between the gap 410 between the two top rollers 320 to view a stent held by the roller assembly 110.

The rollers 310, 320 are configured to avoid damaging a stent while providing a stable surface to rotate the stent thereupon. The rollers 310, 320 may have an outer, rubberized coating to allow the stent 200 to be cradled between the rollers 310, 320 without deforming or compressing the stent 200, and/or without damaging a coating. The rollers 310, 320 may be configured to rigidly support the stent 200 and rotate without distorting, which could cause the rollers 310, 320 to slip against the surface of the stent 200. The rollers 310, 320 are coupled to a drive system 120.

The drive system 120 causes the rollers 310, 320 to rotate at predetermined rates/intervals during imaging with the cameras. The drive system 120 may include a set of four electric motors that are independently controlled by software a software control at the console 20, with each electric motor controlling a separate roller. The drive system 120 may be configured to rotate the rollers 310, 320 in a synchronous manner, and/or to rotate one or more rollers 310, 320 independently from each other. The sequences programmed into the drive system control may be selectively adjusted depending on the sequence of images desired for the stent. The drive system 120 may be controlled at the console 20 to rotate the stent 200 a predetermined amount in order to image different portions of the stent 200 with the camera 140. Thus, the console 20 can coordinate the rotation of the stent 200 with the imaging sequence of the stent 200 by the camera 140.

The drive system 120 may be connected to the roller assembly 110 through flexible drive shafts 340 configured to move with the roller pairs 310, 320 to allow the stent 200 to be loaded and unloaded from the roller assembly 110. The flexible drive shafts 340 may comprise any suitable material and may be of any appropriate dimension, depending on such factors as stent size, diameter, length, etc. The flexible drive shafts 340 may be configured to dissipate ancillary forces that may otherwise be transferred from the drive system 120, causing the rollers 310, 320 to distort.

Figure 6:
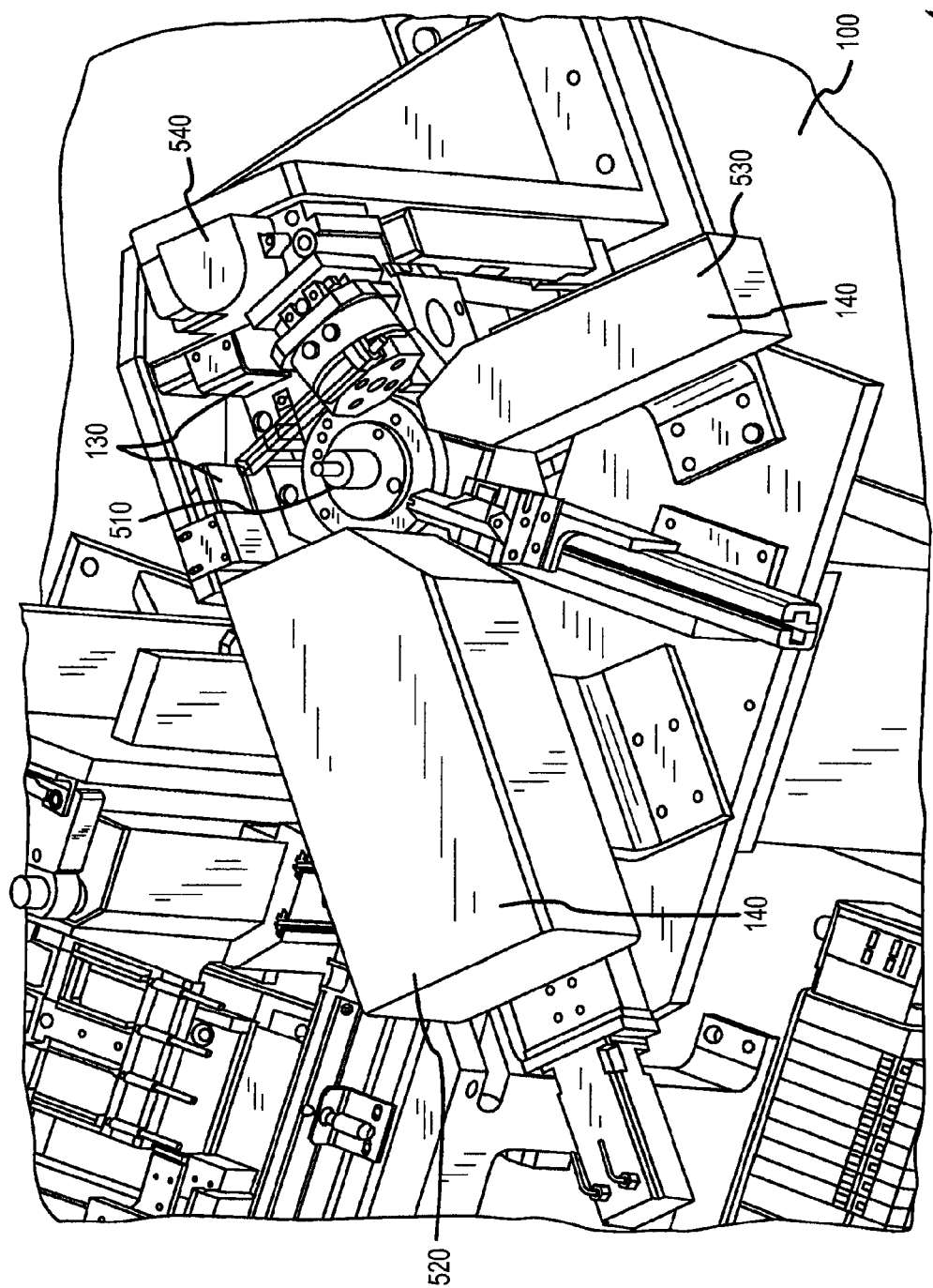
FIGS. 6-7 are perspective views portions of the inspection system of FIG. 1 showing cameras, a base for holding a stent, lights for illuminating the stent and a transfer arm for placing the stent on the base.
Figure 7:
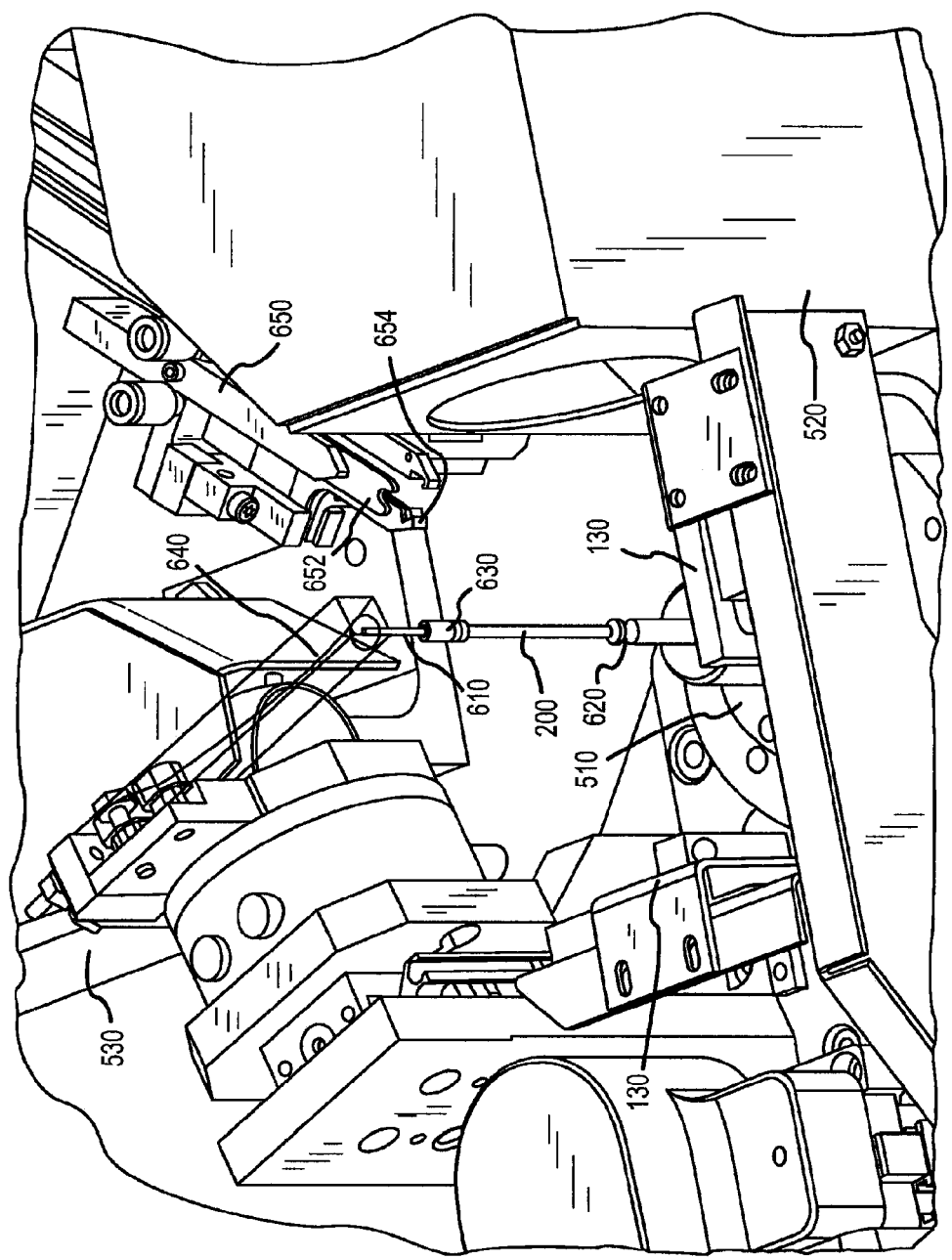
Figure 9:
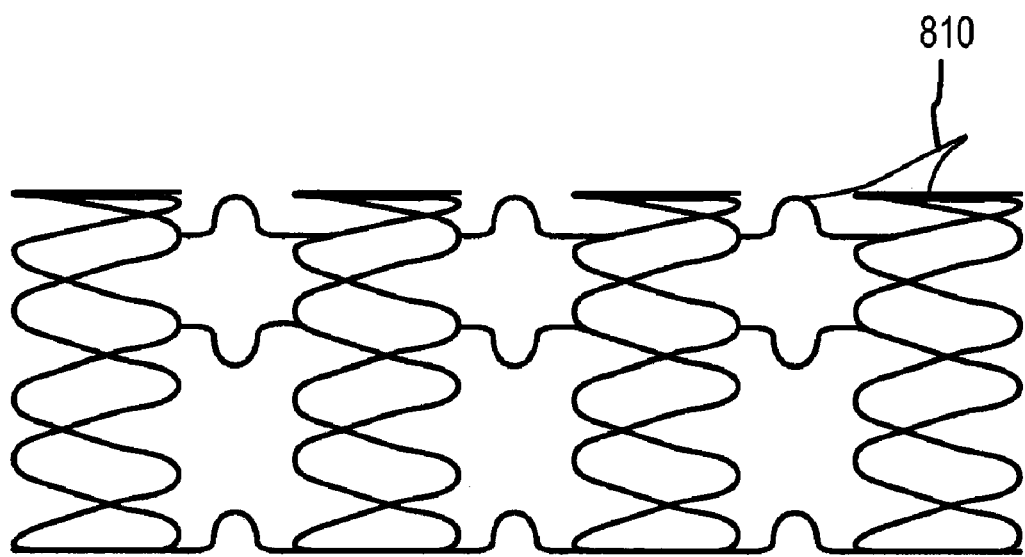
FIGS. 9 and 10 are side views of a stent showing examples of stent defects.

Referring to FIGS. 6-7, a stent may be held by a rotating base 510 to allow defects protruding from the stent 200 to be detected. Such defects are illustrated as bent stent portions 810 and 910 in FIGS. 9-10. The base 510 holds the stent 200 in the field of view of two cameras 520, 530. The base 510 may be raised and lowered using a positioning system 540 to allow the cameras 520, 530 to image the full length of the stent 200. The stent 200 is located between the cameras 520, 530 and light sources 130 that illuminate the boundary edges of the stent 200. As depicted in FIG. 6, the base 510 may hold the stent 200 in place using a mandrel 610 connected to a bottom collet 620. The mandrel 610 is placed through the interior of the stent 200 and a top collet 630 is brought down to capture the stent 200 concentrically around the mandrel 610 by a capture arm 640. The capture arm 640 may also aid in holding the stent 200 and mandrel 610 as the base 510 rotates.

The mandrel 610 may be configured to pass through the stent 200 without contacting its interior so as to avoid damaging the structure of the stent 200 and/or a drug coating the stent 200. The mandrel 610 may be releasable from the top and bottom collets 620, 630 to aid in the transfer of the stent 200 to and from the base 510.

The top and bottom collets 620, 630 engage the stent 200 to hold it in place while it is rotated by the base 510 and imaged by the cameras 520, 530. The collets 620, 630 may engage the stent 200 by inserting a tapered and/or conical end of the collet 620, 630 into the interior of the stent 200 at each end of the stent 200. The base 510 may rotate the stent 200 in 5-degree increments to allow any defects in the stent 200 to be sufficiently imaged by the cameras 520, 530, thereby allowing any defects to be distinguishable from a defect-free stent surface.

Figure 8A:
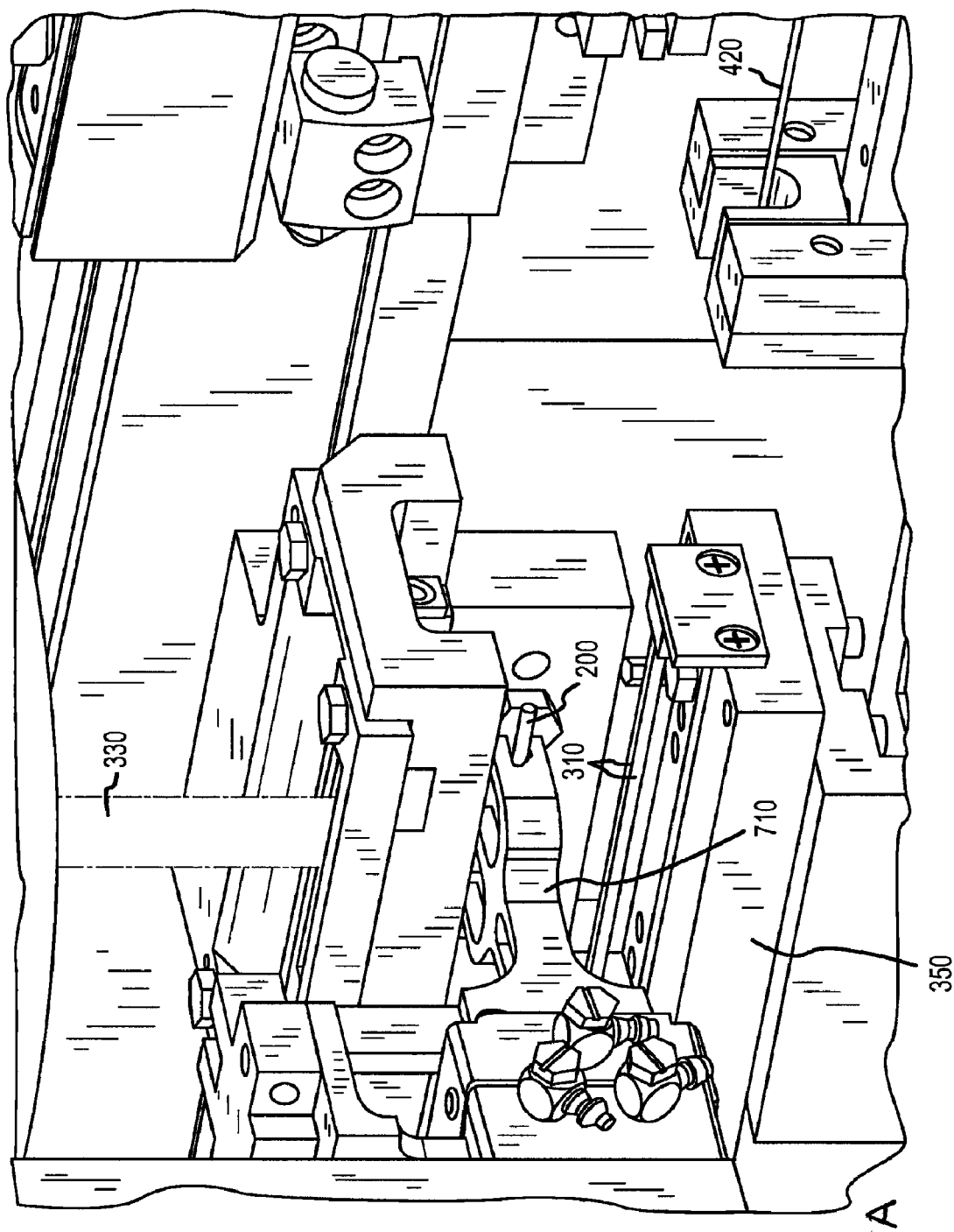
FIGS. 8A-8B are perspective views showing additional aspects of the inspection station of FIG. 1.
Figure 8B:
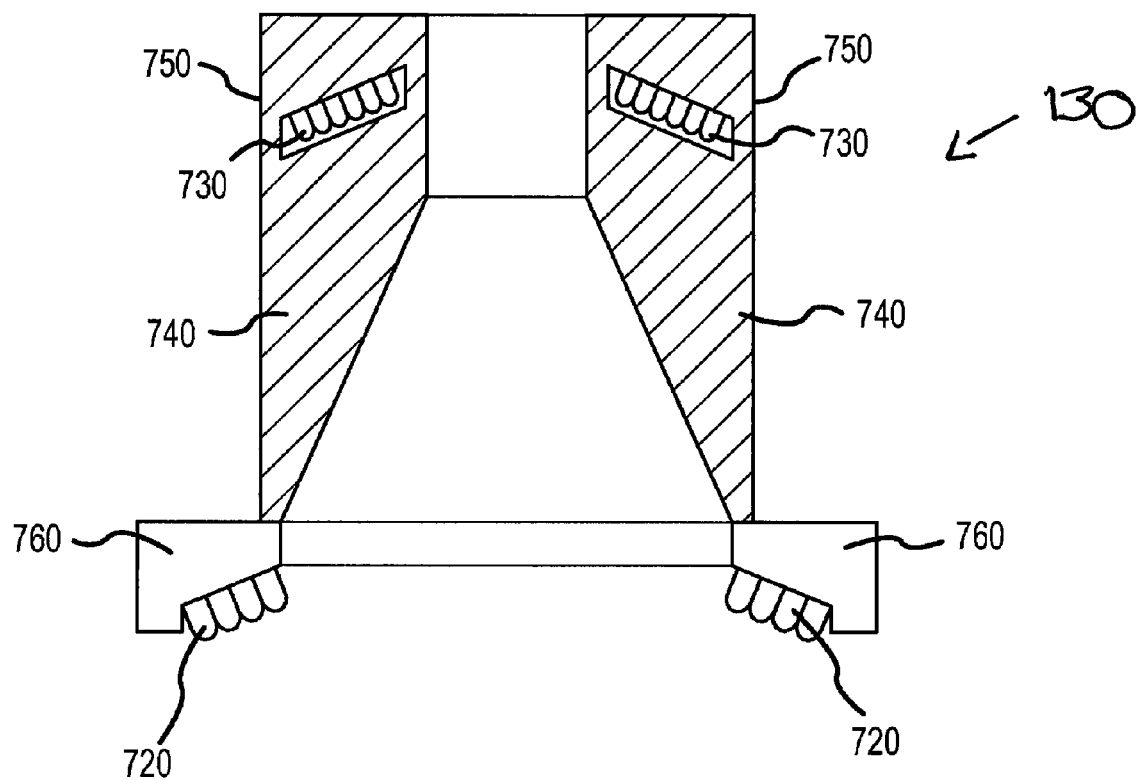

Referring to FIG. 8A, the stent 200 may be moved to and from the roller assembly 110 by a transfer arm 710. The transfer arm 710 may be configured to transfer the stent 200 to other systems and devices, such as other inspection stations. Any number of transfer arms 710 may be employed in an inspection system 100, each having any suitable configuration to manipulate and move the stent 200. Other robotic devices may be employed to automate the inspection of cylinders in an inspection system 100. A stent 200 may be provided to the base 510 by a robotic transfer arm 710, and a capture arm 640 may engage the top collet 630 with the top of the stent 200. The capture arm 640 holds the collet 630 in place to help keep the stent 200 from deforming or otherwise moving on the base 510 as it rotates.

Additionally, a stabilizer arm 650 may be used to automatically position the stent 200 on the base 510. As depicted in FIG. 6, a stabilizer arm 650 may comprise a collet interface 652 and a set of jaws 654. The stabilizer arm 650 may be configured to pick the stent 200 up with the jaws 654 while the stent 200 is on the base 510 and maneuver the stent 200 such that the stent 200 properly interfaces with the bottom collet 620. For example, in the case where a bottom collet 620 comprises a conical surface that engages with the interior of the stent 200 at one end, the stabilizer arm 650 may pick up the stent 200 and drop it over the conical surface of the bottom collet 620 such that the stent 200 properly settles over the bottom collet 620. Similarly, the collet interface 652 may be configured to engage the top collet 630, such as by interfacing with a groove in the top collet 630. The collet interface 652 may lift the top collet 630 up and down to allow a conical surface to engage inside the stent 200. The stabilizer arm 650 may comprise any other suitable structures and devices for manipulating the positioning of a cylinder.

The inspection station 100 includes a light source 130 configured to illuminate the stent for inspection. Referring to FIG. 7B, the light source 130 has a ring light 720 concentrically placed around a dome light 730. An LDR2-90 ring light and an LDM-50 dome light, both from CCS, Inc. may be used. The ring light 720 may surround the stent 200 to provide light to the stent 200 at steep angles, i.e.—nearly parallel to the stent 200, in order to create shadows on the surface of the stent 200 to allow a camera 140 viewing the stent 200 to detect surface imperfections of the stent 200. The ring light 720 may be supported by a light can 760. The dome light 730 may be employed to provide lighting to portions of the stent 200 that otherwise would be left dark by the ring light 720. The dome light 730 may be supported by a light can 750 that includes a translucent material 740 to provide diffuse light from the dome light 730 to the cylinder being inspected. In another exemplary embodiment, referring now to FIG. 5, the light sources 130 may use substantially rectangular lights to provide backlighting for an inspection camera 520 and a focus feedback camera 530.

The light source 130 have other appropriate systems and devices, such as a light source positioning system configured to adjust the position of various elements of the light source 130 to illuminate the stent 200 from various angles relative to the camera 140. For example, the light source positioning system may be configured to allow the dome light 730 to be positioned independently of the ring light 720. The ring light 720 and dome light 730 may be oriented in any appropriate manner to achieve any result. For example, the dome light 730 may be positioned within the ring light 720 to allow the camera 140 to view the stent 200 between a gap between the ring light 720 and dome light 730.

The light source 130 may provide lighting having any desired characteristics, such as wavelength, intensity, and the like. For example, the light source 130 may be configured to provide lighting that is diffuse, that is, light that scatters over a large angular range, in order to avoid glare and/or non-uniform areas of brightness to be viewed by the camera 140 as well as to compensate for a tendency of non-uniform and highly-reflective surfaces on a cylinder to scatter light away from the camera 140. Additionally, the light source 130 may provide light in a specific spectrum in order to avoid affecting a drug or other substance coating a stent 200. In one exemplary embodiment of the present invention, the light source 130 may be specially configured through the use of UV filter to provide lighting having a wavelength of about 600 nm to about 700 nm in order to avoid activating a drug contained within the coating of the stent 200. Preferably, light is filtered to wavelengths less than 390 nm.

The light source 130 intensity, wavelength, and position of the light source 130 relative to the stent 200 may be controlled by the console 20. The ring light 720 and dome light 730 may be independently turned off or on. The ring light 720 may be turned off and the dome light 730 turned on in order to aid in the inspection of the interior of a stent 200. Alternatively, the ring light 720 may be turned on and the dome light 730 turned off in order to aid in the inspection the roughness of the surface of a stent 200 or other cylinder.

The light source 130 may utilize the bearing blocks 350 holding the rollers 310, 320 to help contain the illumination provided by the light source 130 and/or to prevent external light from interfering with the imaging of a cylinder. The light source 130 may be positioned in any manner, such as between the camera 140 and the stent 200 as described previously. Alternatively, referring now to FIG. 5, the inspection station 100 may be configured such that the stent 200 is between a light source 130 and an inspection camera 520, and between another light source 130 and a focus feedback camera 530.

The camera 140 takes an image of a portion of a cylinder for analysis. A linescan camera 140 configured to image a single row of pixels at a time may be used, such as a Dalsa digital line scan camera with a 1.times.6000 aperture. Camera 140 may image any part of the stent 200, features and/or defects protruding from the stent 200, surface irregularities and apertures in the stent surface. The interior of a stent 200 or other hollow cylinder having apertures in its surface may be imaged by the inspection system 100 by moving the camera close to the stent 200, allowing the camera 140 to focus beyond the apertures to view the interior. The images generated by the camera 140 are stored as digital images.

Figure 10:
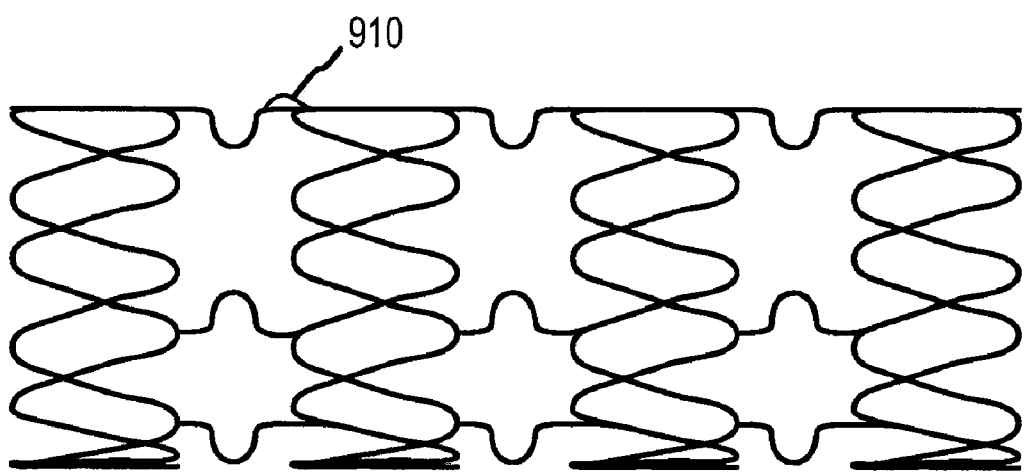

Referring to FIG. 6, two field of view cameras 520, 530, positioned to face ninety degrees from each other, are used to image stent surfaces. The stent 200 is illuminated from behind by the light source 130, which produces a backlight effect that highlights external boundaries defining width/diameter of the stent 200 structure and any irregular features protruding from external boundaries. For example, the image depicted in FIG. 9 indicates a defect 810 protruding from the stent 200. Referring to FIG. 10, a protruding defect 910 may be identified even where the defect 910 is very small relative to the structure of the stent 200. A defect of ten micrometers or smaller may be identified.

The inspection camera 520 may be programmed to create a series of images of the stent according to a sequence. A positioning system 540 may be used to move the base 510 holding the stent 200 along the field of view of the inspection camera 520. The base 510 may rotate the stent 200 a predetermined amount, such as five degrees, to expose a new portion of the stent 200 to the inspection camera 520, and the imaging process can be repeated to image the entire stent. The degree of rotation may be increased or decreased depending on the size of the defects sought to be identified and/or to increase the speed of the inspection process. By simultaneously imaging both edges defining the width of the stent 200 at each position of rotation, the stent 200 can be rotated only 180 degrees while still inspecting the full circumference of the stent 200.

A focus feedback camera 530 can be used to detect any shifting of position by the stent 200 about the mandrel 610, particularly as the stent 200 is rotated. When the stent 200 shifts toward or away from the inspection camera 520, the stent 200 may move out of the focus of the inspection camera 520. The focus feedback camera 530 may be configured to detect a shift in position of the stent 200 and report the shift in position in order to cause the inspection camera 520 to be refocused, or the stent adjusted. The focus feedback camera 530 may be controlled at the console 20 or by software residing at the console. A routine that analyzes an image generated by the focus feedback camera 530, detects a shift in position of the stent 200, and causes the inspection camera 520 to refocus accordingly may be included as part of the imaging sequence.

Figure 5:
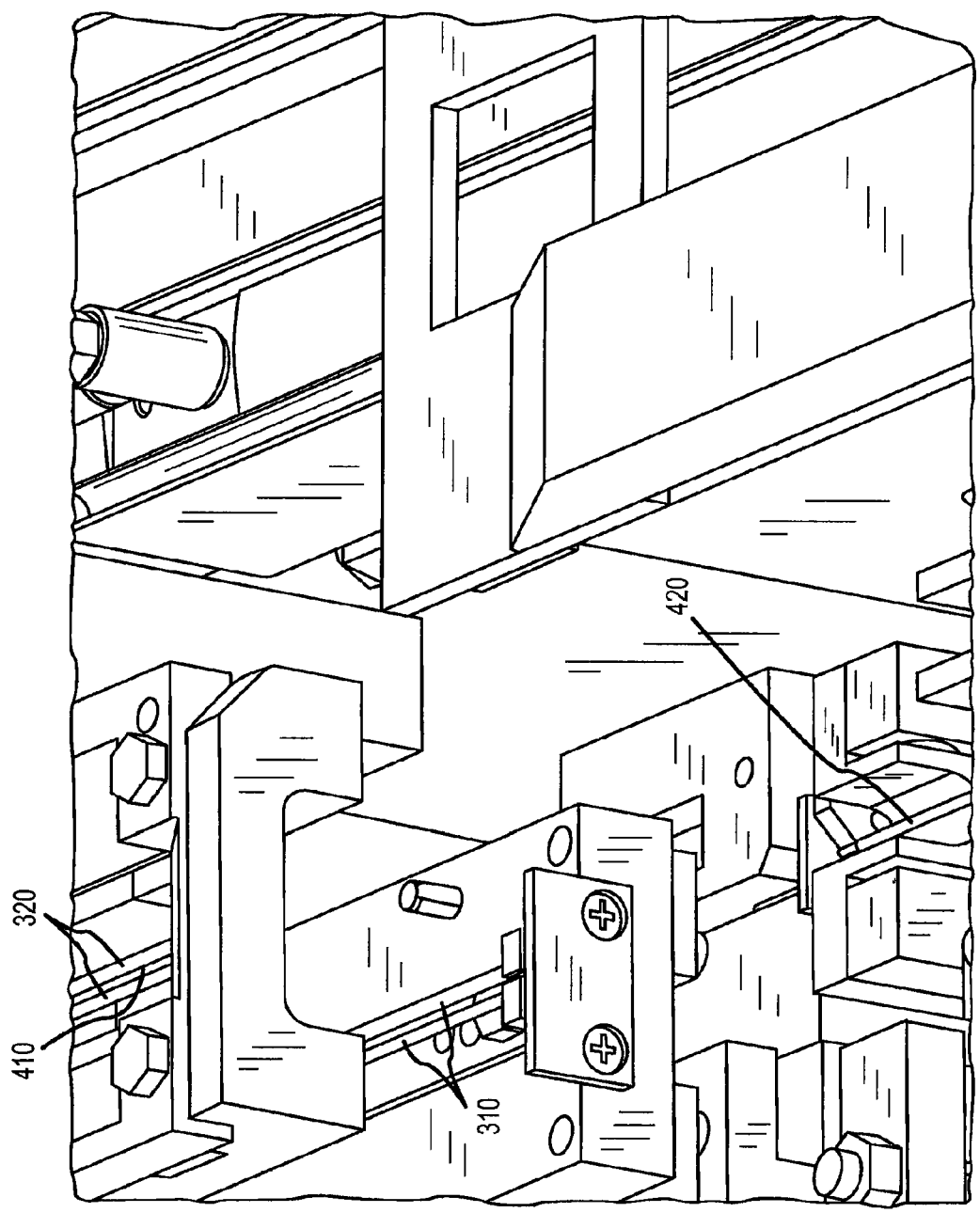
FIG. 5 is a perspective view of a portion of the inspection system of FIG. 1 showing aspects of rollers for supporting a stent.

Referring to FIG. 5, a background mandrel 420 may be used to contrast the stent body form background light. The mandrel 420 is within the bore of the stent 200. The roller assembly 310 in FIG. 4 fully supports and rotates the stent 200 to allow the background mandrel 420 to be disposed within the stent 200 without touching its interior.

Operating software residing at the console 20 may control rotation and positioning of the stent 200 on the roller assembly 110 and/or base 140 during imaging, and one or more cameras 140 in synchronism with the mechanisms rotating the stent in order to take a predefined sequence of images based on the known pattern of the stent retrieved from the database 30. The console 20 may also control the mechanisms for transferring and manipulating the stent 200, such as the wire capture arm 640, stabilizer arm 650, and transfer arm 710 upon operator commands or in an automated fashion after the images have been taken. Included in the imaging process is metadata that indexes images with reference to the position of the roller assembly 110 or base 140 when the image was taken, and/or to stent positions from the stent pattern data so that the images can be easily related back to the stent geometry. Stent pattern data may be taken from the pattern data used to form the stent, from a computer aided design (CAD) or Finite Element Model (FEM) of the stent.

Figure 11:
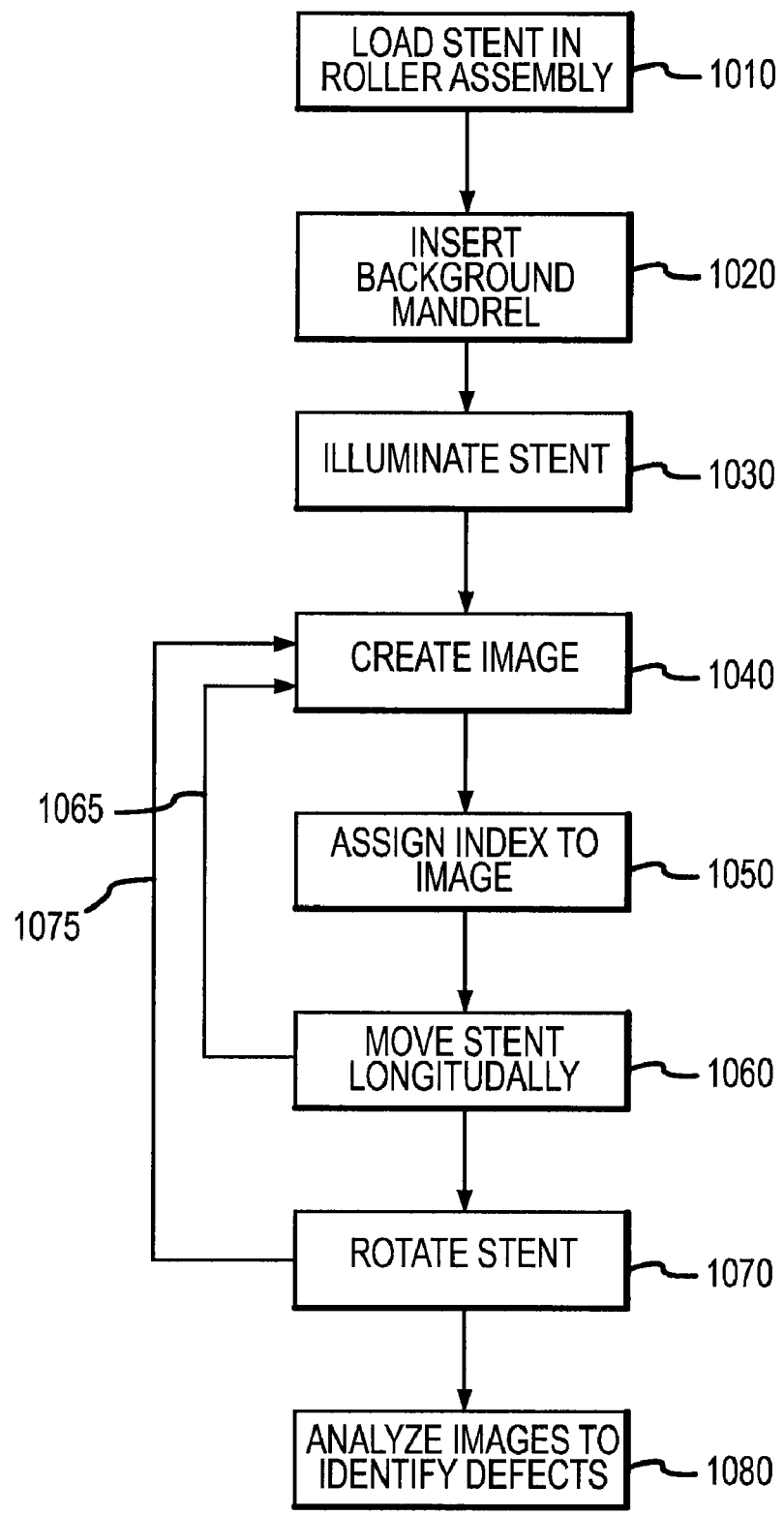
FIG. 11 depicts a first process for collecting images using the stent inspection station of FIG. 1.

FIG. 11 illustrates a process for analysis of the stent 200 to detect defects. A stent 200 is placed on the roller assembly 110 by a transfer arm 710 (1010). A background mandrel 420 is inserted through the interior of the stent 200 to provide contrast between the stent structure and background light (1020). The light source 130 then illuminates the stent 200 (1030) and the linescan camera 140 creates an image of a portion of the stent 200 (1040). The image may be generated by obtaining sequential rows of pixels along a portion of the length of the stent 200. The image is then indexed to the stent pattern data (1050). If the length of the stent 200 is outside the field of view of the camera 140, the camera 140 and/or the stent 200 may be moved to allow the camera 140 to image the full length of the stent 200 (1060). This longitudinal movement may be repeated in order to allow the full length of the stent to be imaged (1065). The stent 200 is rotated by the roller assembly 110 to allow the next sequence of images to be imaged (1070) and the process is repeated (1075) until the entire stent 200 is imaged.

Figure 12:
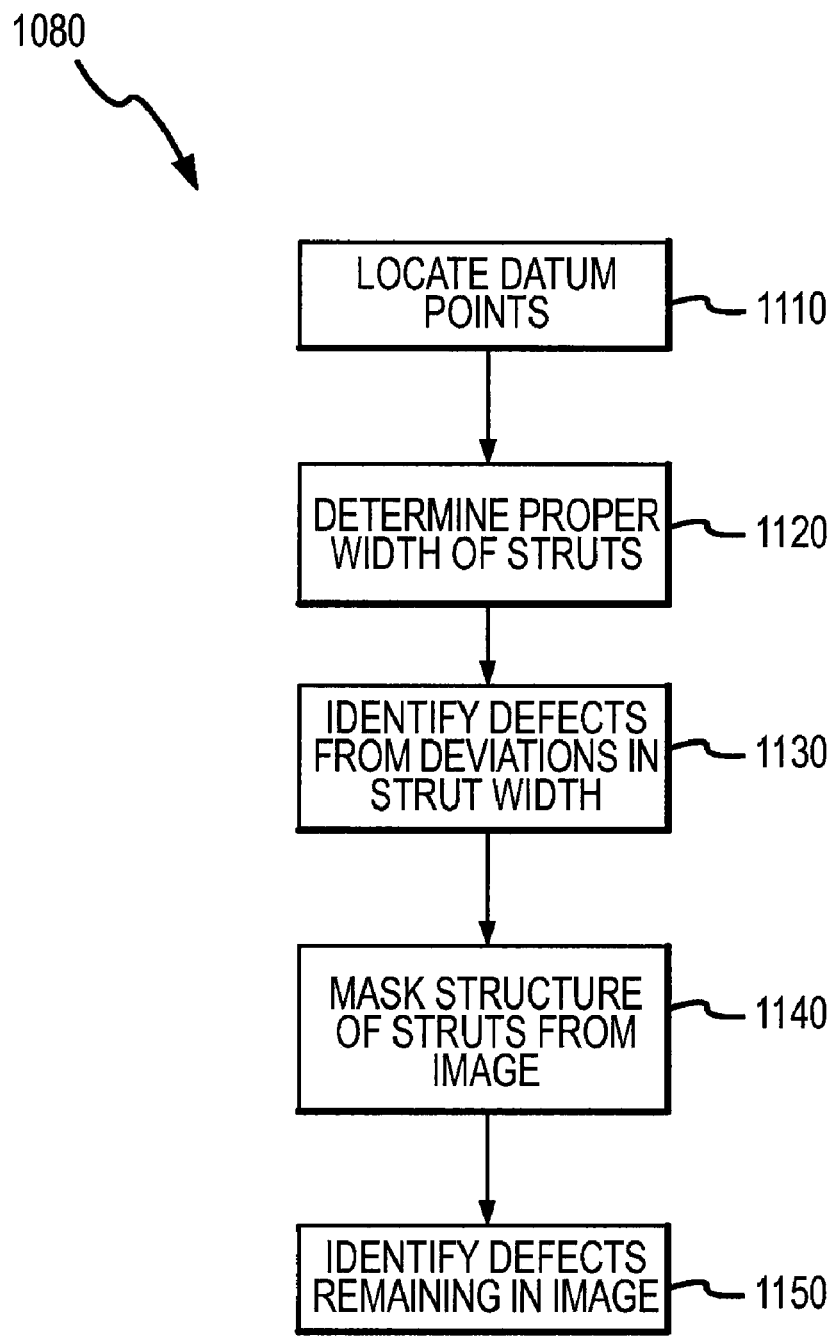
FIG. 12 depicts a first process for finding defects in a stent.
Figure 13:
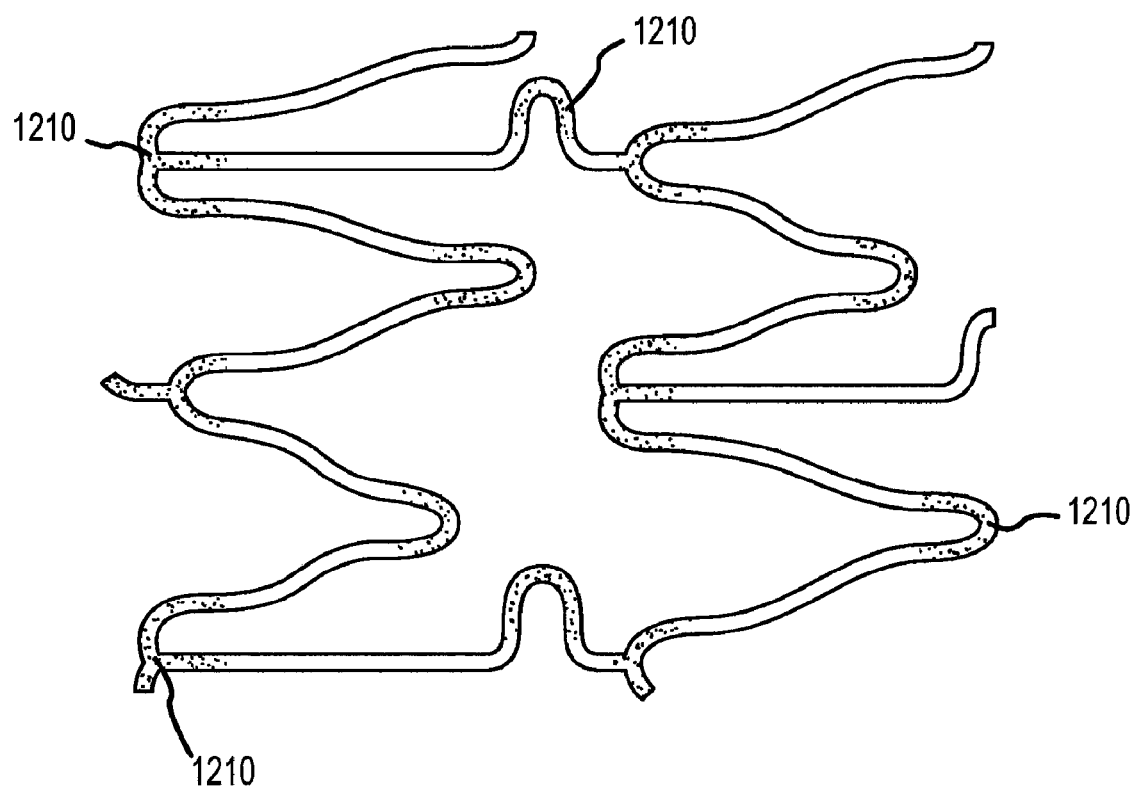
FIG. 13 shows a portion of a planar view of a stent indicating datum points associated with the process of FIG. 12.
Figure 14:
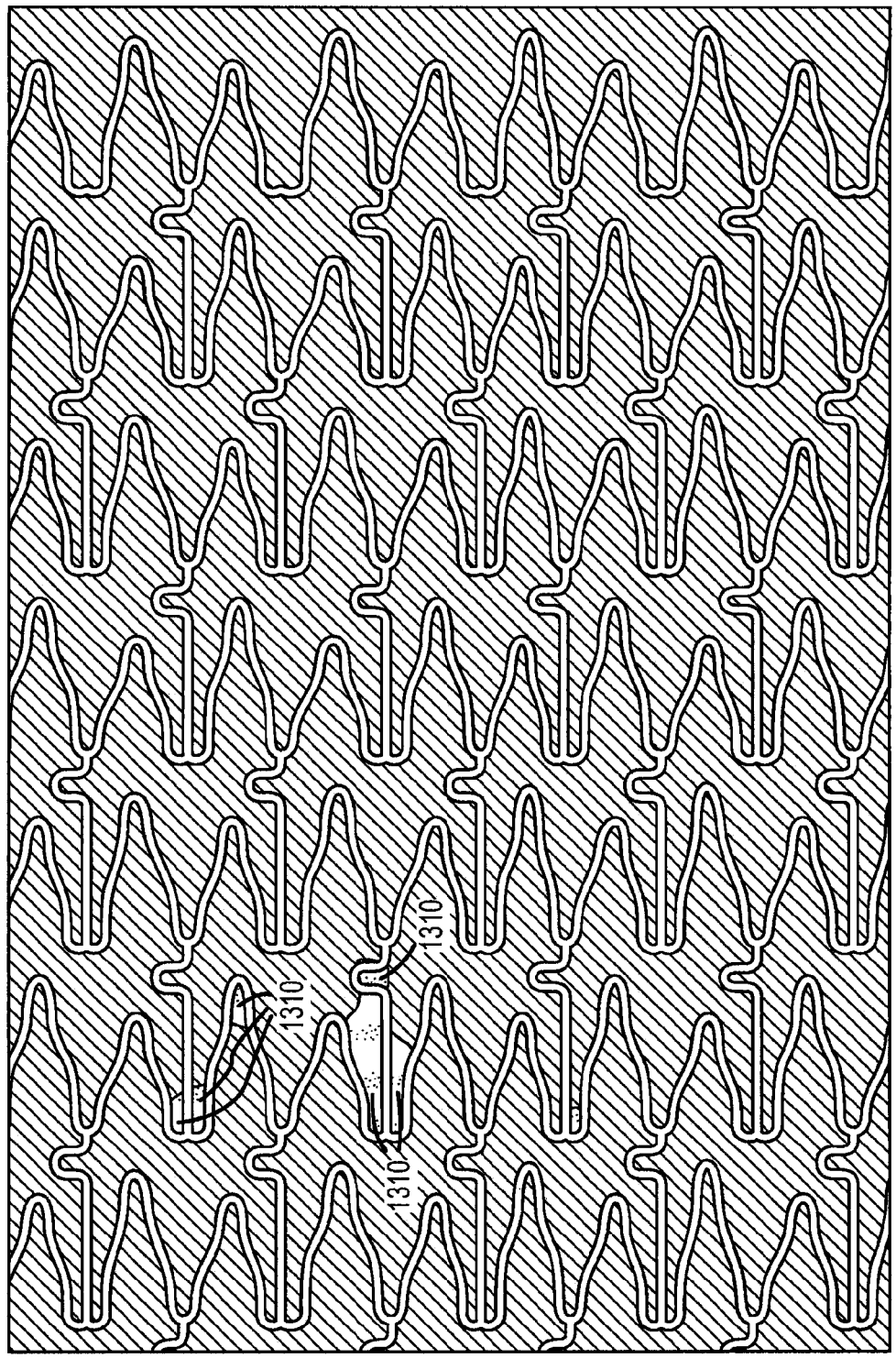
FIGS. 14-15 are views associated with the process of FIG. 12 in which defects are found through masking a stent pattern.
Figure 15:
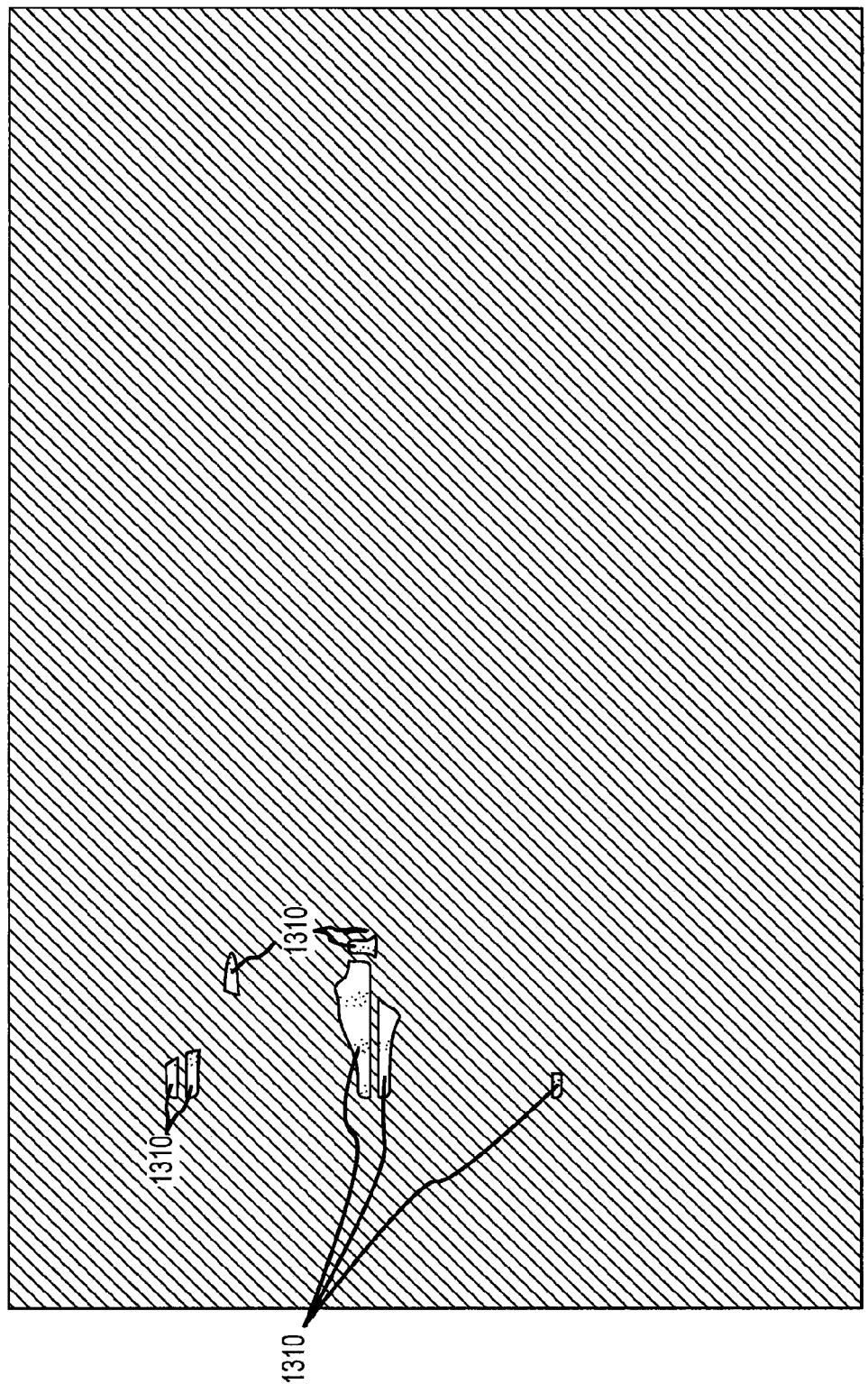

Next, the images are analyzed to identify any defects (1080). FIG. 12 depicts the steps in such a process. A datum is first established (1110). The datum may correspond to, for example, the shaded portions of the struts 210 depicted in FIG. 13. The shaded areas correspond to beginning and ending points of struts 210 in the stent 200. The datum points are used to determine the proper width of struts 210 in the image based on the retrieved pattern and/or dimensions determined from the images at these datum (1120). With the datum defined defects are determined by identifying deviations in the measured width of individual struts 210 in the image (1130). Any other suitable dimension of a feature of a strut 210 may be identified (1120) and analyzed to find defects (1130), such as a strut's 210 height, length, etc. For example, defect analysis (1130) may be performed on a stent 200 to detect a distortion that might have occurred during the manufacturing process, or a surface irregularity. Additionally, defects lying between the struts 210, i.e., webbing from a drug-polymer coating process, may be identified by masking the image of the struts 210 (1140) with the stent pattern and analyzing the remaining features in the image by superposition or differencing the stored pattern with the imaged structure (1150). FIG. 14, for example, depicts a representative image of a stent 200 prior to this masking method. In this image, the struts 210 forming the stent 200 are represented in two-dimensions by a light structure on a dark background. Defects 1310 between the struts 210 of the stent 200 show up as light shading. In order to aid in identifying the defects 1310, referring now to FIG. 15, the structure of the stent 200 is masked out or subtracted from imaged stent, leaving the light-shaded defects 1310 in the image. The structure of the stent 200 may be masked out of an image in any suitable manner.

Figure 16:
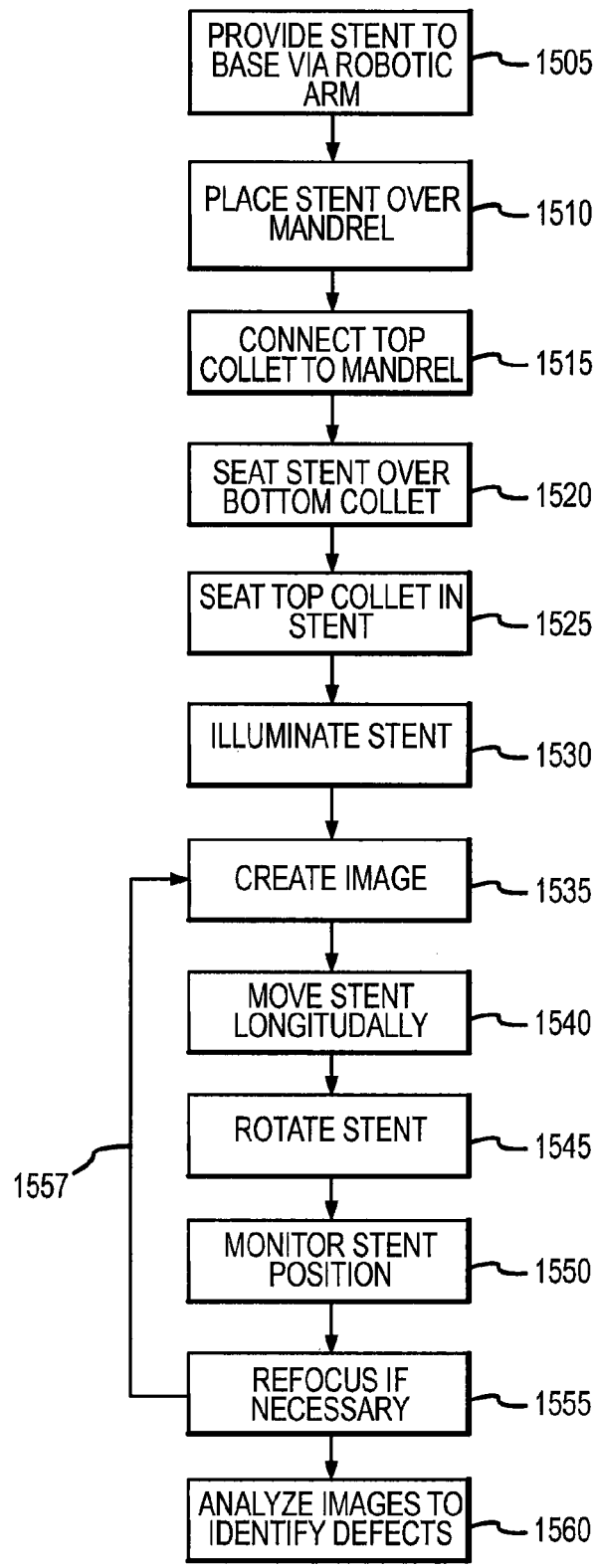
FIG. 16 depicts a second process for collecting images using the stent inspection station of FIG. 1.

An alternative process for finding defects is illustrated in FIG. 16. The stent 200 is automatically transferred to the base 510 by the transfer arm 710 (1505). The stent 200 is placed over the mandrel 610 connected to a bottom collet 620 (1510). A wire capture arm 640 brings a top collet 630 in connection with the mandrel 610 (1515). A stabilizer arm 650 grasps the stent 200, then lifts and releases the stent 200 to cause it to settle over a conical surface on the bottom collet 620 (1520). When properly settled, the interior of the stent 200 engages the conical surface of the bottom collet 620 without the stent 200 touching the mandrel 610. The stabilizer arm 650 interfaces with the top collet 630, lifting and dropping the top collet 630 to cause a conical surface on the top collet 630 to settle into the interior of the stent 200 (1525).

With the stent 200 engaged by the top and bottom collets 620, 630, the stent 200 is positioned between two light sources 130 and two cameras 140, 520, 530, where each light source 130 illuminates the stent 200 from behind each camera 520, 530 (1530). The inspection camera 520 creates an image of the stent 200 that includes the full width of the stent 200 and features protruding from the edges of the stent 200 (1535). The base 510 moves up and down to allow the inspection camera 520 to create images along the full length of the stent 200 (1540). The base 510 rotates the stent 200 a certain amount, such as 5 degrees, to expose a new portion of the stent 200 to the inspection camera 520 (1545). The focus feedback camera 530 monitors whether the stent 200 changes position on the mandrel 610 at any point during the imaging process (1550). If a change in position is detected, the inspection camera 520 is refocused accordingly (1555). The inspection camera 520 may be refocused in any suitable manner, such as by adjusting a focus control in the camera 520, physically moving the camera with relation to the stent 200, and the like. The process may be repeated (1557) in order to capture images of the full diameter of the stent 200. Since both edges of the stent 200 are being captured in a single image, the stent 200 need only be rotated 180 degrees to image the full diameter of the stent 200.

Figure 17:
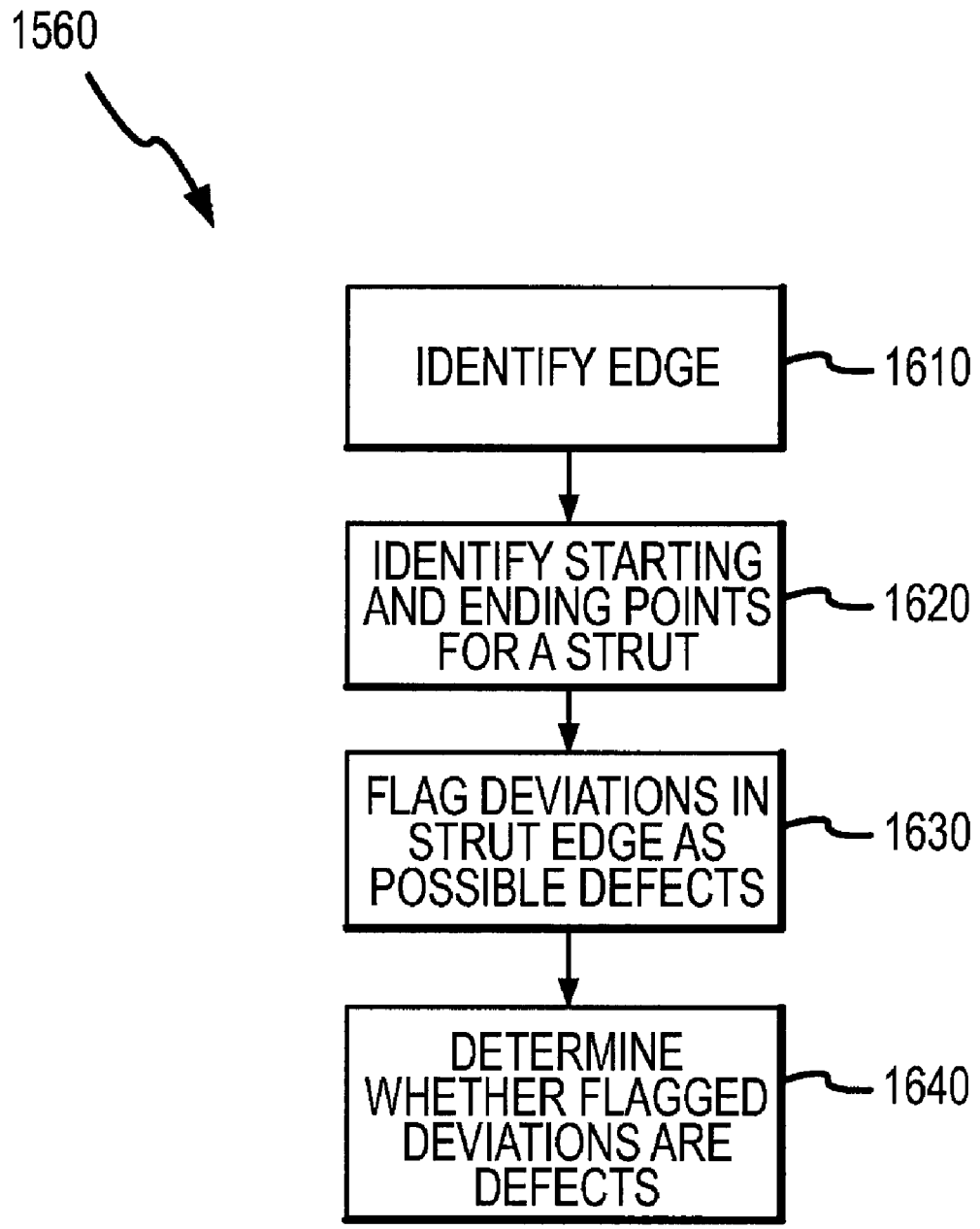
FIG. 17 depicts a second process for finding defects in a stent.

The images are then analyzed to identify defects protruding from the stent 200 (1560). A process for analyzing an image for protruding defects (1560) is illustrated in FIG. 17. An approximate edge location is identified from the image (1610). For each strut 210 comprising a portion of the edge, a starting position and an ending position is identified (1620). These reference dimensions or lines may be located from the stent patterns stored in the database 30. The line between the starting position and ending position defining the edge of a strut is analyzed and any deviations from the reference line, and within the defined tolerances (i.e. height, length, and area) are flagged as defects (1630). For each deviation flagged as a potential defect, a determination is made as to whether the deviation is part of the structure of the stent 200 that should be considered a defect requiring further inspection (1640). For example, a deviation found near the edge of the strut may be analyzed to determine the relative size of the deviation compared to other features in the image to determine whether it should be flagged as a defect requiring inspection. A non-linear link (curved) portion of a strut can be examined in the same manner as linear (straight) sections 1810 using the stent pattern data, as will be appreciated. U.S. Pub. No. 2008/0312747 provides additional examples of detecting defects based on images without the aid of stent pattern data.

Structure defects, such as cracks, bending, warping, irregular coating, clumps, webbing may be identified by either of the foregoing processes. In the case of irregular or non-uniform polymer coatings the analysis may perform a difference in shades of gray over the stent surface. Defects may be found by analysis of a single image or multiple images processed together. The locations and spatial characteristics, i.e., size, shape, differences in shades of gray, etc. of found defects are indexed according to the locations where they are found.

In one embodiment images are organized into a dataset or record that includes header or metadata information, such as the type of stent, location where a defect was found, type of defect, whether other defects were found or were found in the same structural member or nearby/adjacent areas to the defect described in the record, type of stent material, the intended use of the stent, how the stent was made, etc. in a format that enables an automatic query of the relational database for samples of previously inspected stents that had defects accepted or rejected. The metadata information may also guide the inquiry of whether a certain heuristic rule, safety factor or other decision criteria should apply (in addition to the decision process based only upon the spatial characteristics of the defect and where it is located).

Figure 18:
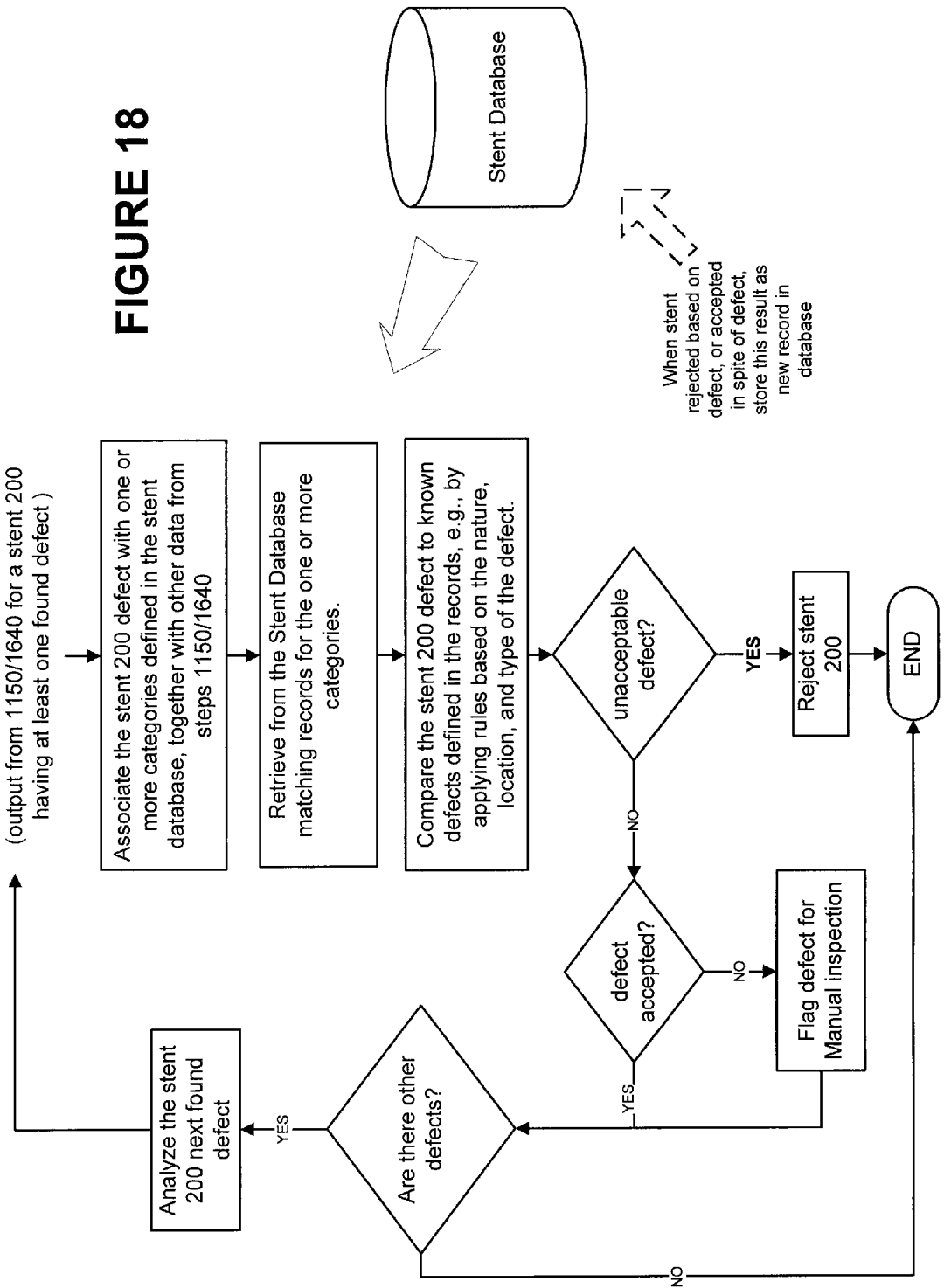
FIG. 18 is a diagram depicting a process for accepting or rejecting a stent.

A process for deciding whether to accept or reject a stent having a defect is now discussed. The process begins after defects in an imaged stent, such as stent 200, are indexed, categorized and classified based on relational database information (as discussed above). FIG. 18 presents a flow diagram of one embodiment of a process for automated determination of whether to reject or accept a stent. The process includes the step of determining, using knowledge contained in database 30 and information derived from the imaged stent whether a stent should be rejected based on one or more found defects, or accepted in spite of the presence of defects. A computational analysis and/or logic, e.g., heuristic rules, is implemented to at least assist the technician with making a decision of whether to accept or reject the stent.

The image data for the stent under inspection, specifically the information that describes defects found in the stent, is, as was explained above, supplemented with metadata that enables the found defect to be associated similar defect information from previously inspected stents. This information is organized into a relational database, which in FIG. 1 is referred to as libraries of known defects, e.g., "libraries of known forming defects". The relational database is structured according to the list of categories complimentary to the information about the stent's defect provided in its metadata or header record as discussed above. That is, the type of stent, location where a defect was found, type of defect, whether other defects were found or were found in the same structural member or nearby/adjacent areas to the defect described in the record, type of stent material, the intended use of the stent, how the stent was made, etc. so that the database may be queried based on input including one or more of these categories, classes or groups of data. Ultimately, it is expected after a sufficient number of samples have been collected for each group, that statistics may be possible that can be used to reach a decision or confirm a conclusion based on another method or the technician's own judgment.

For example, when a crack is found in a particular crown of a stent Type A, this location and defect type information for the stent may be used to query the relational database for all known information about previously inspected Type A stents that contained similar cracks at this location, including whether a similar crack found in previous stents were accepted or rejected. The TABLE, below, illustrates an example of an organization for the relational database.

TABLE

Previously inspected defects for Stent Type A (FIG. 2C)

| Stent Type | Location | Mfr Stage | Defect Type | Previously inspected stents having similar defects |
|---|---|---|---|---|
| TYPE A | | | | |
| | Crown A6 | | | |
| | | forming | Bending | |
| | | | | {rejected(1), rejected(2), rejected(3) ... rejected(p)} {accepted(1), accepted (2), accepted (3) ... accepted (q)} |
| | | | Crack | |
| | | | ... | ... |
| | | coating | webbing | |
| | | | | {rejected(1), rejected(2), rejected(3) ... rejected(r)} {accepted(1), accepted (2), accepted (3) ... accepted (s)} |
| | | | Clumping | |
| | | | ... | ... |
| | Crown F6 | | | |
| | ... | ... | ... | |

The database has associated with it a search module that receives as input query requests and performs searches of the database to return records matching the parameters of the query. The database 30 also may include a module that allows the database to be periodically updated with new information, such as when a defect new to the database has been evaluated and a stent rejected/accepted in view of this defect.

For example, referring again to the TABLE, if the stent 200 is a "TYPE A" stent that was recently laser-cut from a tube, and a bent member was found at location "Crown A6" (see FIG. 2B), then a query of the database, e.g., submitting the call search(stent type="TYPE A", location="Crown A6", mfr stage="forming", defect type="bending") returns "p" number of samples, Reject(i), i=1, 2, . . . p, of "Type A" stents having bending at "Crown A6" that were rejected, and "q" number of samples, Accept(j), j=1, 2, . . . , q, of "Type A" stents having bending at "Crown A6" that were accepted. The records may include values that characterize the nature of the bending that was found. For example, Reject(i) may include values that provide a length, width and location along the arc of the crown where the bending for a previously rejected Type A stent was found (based on the presence of this bending). Similarly, Accept(j) may include values that provide a length, width and location along the arc of the crown where the bending for a different, accepted Type A stent was found, meaning the stent was accepted despite the presence of this bending.

Similarly, if the stent 200 is a "TYPE A" stent that was recently spray coated to form a drug-polymer layer on the stent surface, and webbing was found at location "Crown A6" (see FIG. 2B), then a query of the database returns "r" number of samples, Reject (i), i=1, 2, . . . r, of "Type A" stents having webbing at "Crown A6" that were rejected, and "s" number of samples, Accept(j), j=1, 2, . . . , s, of "Type A" stents having webbing at "Crown A6" that were accepted. The records may include values that characterize the nature of the webbing that was found. For example, Reject(i) may include values that provide a length, width, thickness along the arc of the crown where the webbing for a previously rejected Type A stent was found (based on the presence of this webbing). Similarly, Accept(j) may include values that provide a length, width, thickness and location along the arc of the crown where the webbing for a different, accepted Type A stent was found, meaning the stent was accepted despite the presence of this webbing.

Referring now to the case of stent 200 having a bending defect at Crown A6, the data in the p and q number records is used to determine whether the stent 200 should be rejected or accepted in spite of the bending defect at Crown A6. While this determination may be straightforward if the same bending defect was previously found in a previously rejected or accepted stent, or a characteristic value is less than or greater than one for a previously inspected stent defect, e.g., root mean square of the maximum extent in three dimensions for the bent strut portion, in general the bending will not fall totally within all acceptance or rejection criteria (e.g., the bending is neither insignificant nor too large to reach a decision based on prior inspections of bent crowns). So consideration is given as to how to evaluate a bending defect that was not previously encountered, if possible. With this in mind, referring to FIG. 18, there may therefore be three possible outcomes for an automated inspection process: the defect is unacceptable and the stent is discarded, the defect is acceptable, or a determination cannot be made to accept or reject the stent based on the defect, in which case the defect is flagged for manual inspection following termination of the automatic inspection process.

The evaluation of a defect when a defect was not identically encountered in a previously inspected stent may simply be avoided by flagging the defect for manual inspection (FIG. 18), or a computation made to determine, to an acceptable degree of confidence, that the defect is, or is not acceptable. An algorithm or statistic chosen may be a function of parameters that derive from the unique considerations inherent in the evaluation of a medical device, such as stents, as opposed to another product of manufacture, to best ensure that when implanted within a body no complications will arise as a result of the defect, e.g., broken strut, irregular drug release profile, improper placement, etc., or so that stents won't be discarded for minor defects. It is understood that a manual inspection of stents may nevertheless be required in some cases. According to one embodiment, if the defect is not sufficiently similar to a prior defect encountered, e.g., it is not found in one of the rejected(i) or accepted(j) sets in the TABLE within a proscribed range, then the defect is flagged as requiring a manual inspection.

While there are some defects that are different from others encountered in past inspections, it has been discovered that there are nonetheless several varieties of defects recurring, or exhibit characteristics that assures the defect can be judged as acceptable or not acceptable using computational or rule-based algorithms. The empirical evidence therefore revealed a solution to the well recognized yet, until now, intractable labor problem. Surprisingly and unexpectedly, through realization of certain subtle defect characteristics that happen to periodically re-occur during stent inspection, a solution was finally found that addresses the unsolved need for reducing cost and manpower burdens heretofore assumed a necessary part of stent manufacture.

Indeed, according to one aspect of the invention, this sharp reduction in costs and man hours is significant even if there remains a frequent need to perform a manual inspection for defects not suitable for automated inspection. For example, if there are 10 defects and 5 are found by an automated method, then the inspection time is cut in half, and likely greater than one half, as will be appreciated by considering the related advantages of invention, which further reduce burdens on an inspecting professional—thereby increasing efficiency and reducing errors. For example, the automated inspection may, with regards to these 5 undecided defects, be programmed to produce information informing the technician of the characteristics/reasons why a result was not found. The technician may then more quickly reach a decision as to whether the defect should be rejected or accepted in spite of the defect.

Savings may also be found in a relational database that, while not automatically deciding whether to accept or reject a medical device, uses information learned from past defect inspection to guide a manual inspection. In this sense, the inspection system may identify all areas that have previously resulted in a defect being unacceptable. The technician then chooses whether to reject or accept the device by visually inspecting the areas brought to his/her attention.

Based on the empirical data, and/or in connection with analytical studies, heuristic rules may be developed to reject a stent when a defect is irregular, i.e., different from previously encountered defects that were either rejected or accepted. One may proscribe, for example, the following set of heuristics rules:

whenever a crack or fracture extends beyond a predefined length at or near a high stress area (i.e., a bend or crown) then the stent is rejected;

when a surface area of the webbing extending between stent members is beyond a predefined surface area then the stent is rejected;

when a strut touches another strut the stent is rejected;

when bending causes a strut to extend beyond the abluminal stent surface by a predefined amount, the stent is rejected;

when an opening in the coating exposes an underlying metal surface exceeds a specified acceptance criteria for an exposed surface, the stent is rejected;

when a coating peels or tears, and is found to exceed an allowable size of tear/peel then the stent is rejected;

when a polymer strand exceeds an allowable amount for a polymer strand the stent is rejected;

when a rough surface finish exceeds the required level of smoothness needed for a surface, e.g., a metallic or polymer surface receiving a polymer coating, then the stent is rejected;

when a foreign material is found in the base material that cannot be removed using an air gun, and exceeds an allowable size/volume then the stent is rejected;

when a stent exhibits a sharp point/edge that exceeds a smoothness criteria then the stent is rejected; and when stent struts overlap the stent is rejected.

As will be appreciated, other heuristics may be defined. According to one aspect, a database includes the above heuristics appropriately applied to a stent following a forming or coating stage or phase. Other heuristics may be applied for inspection following, e.g., a crimping stage or mounting stage on a catheter.

The rules may incorporate factors of safety, e.g., multiple the crack length derived from the digital image by 2 when evaluating this type of defect. A rule may be based upon a simultaneous comparison of several defects at the same time, e.g., bending of two or more adjacent struts appearing at different stent locations. A rule may evaluate a root-mean-square value for the maximum extent of a defect in three dimensions (which can be calculated from the image data) and then compare this value to the root mean square values for previously rejected and accepted stents having a similar defect. Acceptable defects might be thus defects whose RMS value lies within this, e.g., spherical volume of acceptable defects.

Statistics for evaluating defects may be developed in different ways. After it has been determined that a sufficient number of samples are available, e.g., a sufficient number of stent defects evaluated, results recorded and categories developed to define sample spaces based on the types/characteristics of sample stent defects, a statistical significance test may be run over defined sample spaces, e.g., cracks, or cracks at crowns, etc., to determine what combination or value strongly correlates with a rejection or acceptance. For example, a crack length less than or greater than a certain value might correlate strongly with the acceptance or rejection of a stent having a crack at a crown.

Assuming sufficiently-sized sample spaces, a Gaussian distribution may be assumed and a mean and standard deviation derived. Thus, in the case of a forming defect being a crack, a first probability distribution having a mean and standard deviation is used to represent the probability that a crack length exceeds an acceptable length, and a second probability distribution is used to represent the probability that a crack length is not a concern. When a crack is encountered, the value may be compared to the three sigma interval about the mean derived for the first distribution (to decide whether the stent should be rejected) and the three sigma interval about the mean derived for the second distribution (to decide whether the stent should not be rejected, in spite of the crack). The mean for the first distribution may be the average minimum crack length that resulted in a stent being rejected based on a measured crack length. The mean for the second distribution may be the average maximum crack length that resulted in the stent being accepted in spite of the crack. Values that are greater than $(\mu+3\sigma)_{accepted}$ but less than $(\mu-3\sigma)_{rejected}$, however, are flagged for manual inspection (the quantities $(\mu+3\sigma)_{accepted}$ and $(\mu-3\sigma)_{rejected}$ refer, respectively, to the sum of the mean and three-times the standard deviation from the second distribution and the difference of the sum and three-times the standard deviation for the first distribution). Thus, on the one hand, if a measured crack length is less than $(\mu+3\sigma)_{accepted}$ then a stent may be deemed acceptable in spite of the crack. On the other hand, if the crack length is greater than $(\mu-3\sigma)_{rejected}$ then the defect may be deemed unacceptable and the stent rejected. Values that fall in-between provide no information (manual inspection required). Alternatively, in other examples rather than using a crack length, probability distributions may be based on RMS spatial values or approximate crack volumes.

As stents are inspected and defects accepted or rejected, these results may be added to the relational database, which improves the robustness of the automated inspection. This database update step may be considered as an additional step associated with inspecting a medical device, in some embodiments of the invention. In one example, the relational database may be programmed, or contain an ancillary structured database, or knowledge base for learning new rules as a technician evaluates new defects. For example, in one example an evaluation algorithm may identify characteristics of a defect not previously encountered, e.g., a new bending shape for a strut (indicating a potential problem) but relatively minor excursions into the abluminal surface of the stent. If not for the abnormal bending, the algorithm would have accepted the defect, or if the excursion was greater it would have rejected the stent. The monitor screen flags the defect for manual inspection. The technician, when performing this manual inspection is notified that the stent was not accepted because the existence of a bending pattern previously not seen. The technician, when seeing this pattern reaches a conclusion—either reject or accept the stent—and records these results. This result may then be stored for later incorporation into the relational database as a rule for rejecting/accepting similar defects, or to inform/confirm conclusions during future inspections. Accordingly, new rules may evolve over time.

Although stored samples of defects arising from, e.g., abnormal bending shapes, which was the deciding factor to reject or accept the stent, may not, in general, be used as a data point to construct a hierarchy of rules covering all, or most, future defects, storing this type of information into the database can nevertheless be very useful. For instance, by storing this result, a manual or human judgment-based decision may be automatically subject to quality control, meaning others would review and confirm the result. Then, by assigning a category for this category of defect, e.g., bending shapes having curvature about more than one axis, future, similar defects encountered by a technician performing manual inspection can verify his/her result, guide him/her, teach, etc. by comparing the defect to the previously rejected or accepted defect within this class of defects. As such, in some embodiments an automated inspection system reduces man-hours by highlighting to the technician the areas that in the past have caused a stent to be rejected/accepted, while leaving the ultimate decision up to the technician. The more straightforward defects are reviewed automatically. Additionally, there is enhanced quality control, and the system can also serve/function as a teaching or training platform.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A computer-based method for inspecting a polymeric stent, comprising:
   (a) collecting images showing a portion of the polymeric stent;
   (b) finding a defect in the portion by computer analysis of the collected images;
   (c) retrieving samples of defects from previously-inspected polymeric stents, wherein the defect samples include unacceptable defects found in polymeric stents that were rejected and acceptable defects found in polymeric stents that were accepted; and
   (d) comparing the found defect to both the acceptable defects and unacceptable defects including computing at least one number and, based on this comparison, deciding whether to accept, reject or manually inspect the polymeric stent;
   wherein the comparing step further includes simultaneously comparing several found defects including bending of two or more adjacent struts appearing at different polymeric stent locations and deciding, based on this comparison, whether to accept, reject or manually inspect the polymeric stent; and
   wherein the bending of two or more adjacent struts includes at least one of a pair of struts being bent so that the two struts touch each other, a pair of struts being bent so that they overlap each other, or two or more struts that extend beyond the abluminal surface of the polymeric stent by a predefined amount.

2. The method of claim 1, wherein the comparison step includes computing a characteristic value that represents a severity of the several found defects in the polymeric stent, and the accepting or rejecting step includes accepting or rejecting the polymeric stent if the value falls within or outside, respectively, of a range of predefined polymeric stent defect characteristics.

3. The method of claim 2, wherein the defect characteristic is selected from the list consisting of polymeric stent type, location where a defect was found, magnitude of one or more spatial characteristics of the defect, the presence of other defects or lack thereof, and the sufficiency of samples for generating statistics associated with acceptable or unacceptable defects.

4. The method of claim 1, wherein the at least one number is a root mean square of values representing spatial excursions associated with the several found defects, and the comparison is with similar root mean square values from the defect samples.

5. The method of claim 4, wherein the comparison further includes evaluating a heuristic rule based at least in part on where the defect occurred, the type of polymeric stent and/or the type of material in the polymeric stent.

6. The method of claim 1,
   wherein the comparing step further incorporates a pass-fail logic for inspecting cracks in the polymeric stent, the pass-fail logic including a first rule that accepts a crack having a predefined length when that crack is not located at a crown of a stent and rejects the stent when the crack having the predefined length is located at the crown.

7. The method of claim 6, wherein the pass-fail logic includes heuristic rules developed from pass-fail patterns derived from empirical evidence of polymeric stents that were rejected and polymeric stents that were accepted.

8. The method of claim 1, wherein the comparing the several found defects to defect samples includes comparing the several found defects to a first statistic and a second statistic and based on this comparison deciding whether to accept, reject or manually inspect the polymeric stent,
   wherein the first statistic is computed from a collection of acceptable defects found in previously inspected polymeric stents that were accepted in spite of the defect, and
   wherein the second statistic is computed from a collection of unacceptable defects found in previously inspected polymeric stents that were rejected.

* * * * *